(12) United States Patent
Pindl et al.

(10) Patent No.: US 11,211,298 B2
(45) Date of Patent: Dec. 28, 2021

(54) SYSTEM AND METHOD FOR A TRANSDUCER IN AN EWLB PACKAGE

(71) Applicant: Infineon Technologies AG, Neubiberg (DE)

(72) Inventors: Stephan Pindl, Ergoldsbach (DE); Daniel Lugauer, Altenthann (DE); Dominic Maier, Pleystein (DE); Alfons Dehe, Villingen Schwenningen (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 16/654,165

(22) Filed: Oct. 16, 2019

(65) Prior Publication Data
US 2020/0051824 A1 Feb. 13, 2020

Related U.S. Application Data

(62) Division of application No. 16/227,761, filed on Dec. 20, 2018, now Pat. No. 10,546,752, which is a
(Continued)

(51) Int. Cl.
*H01L 23/053* (2006.01)
*H01L 21/20* (2006.01)
(Continued)

(52) U.S. Cl.
CPC ......... *H01L 23/053* (2013.01); *G01N 27/028* (2013.01); *G01N 27/128* (2013.01);
(Continued)

(58) Field of Classification Search
CPC ....... H01L 23/04; H01L 23/041; H01L 23/10; H01L 23/31; H01L 23/3157; H01L 23/3192; H01L 21/306; H01L 33/0093; H01L 21/76256; H01L 21/02016; H01L 21/302; H01L 23/057; H01L 23/315; H01L 23/3107; H01L 23/053; H01L 23/296; H01L 24/19; H01L 24/24; H01L 24/96; H01L 21/2007; H01L 21/185; H01L 21/187; H01L 21/7624; H01L 21/561; H01L 23/3128; H01L 23/5386;
(Continued)

(56) References Cited

U.S. PATENT DOCUMENTS 5,353,498 A 10/1994 Fillion et al.
6,002,592 A 12/1999 Nakamura et al.
(Continued)

FOREIGN PATENT DOCUMENTS

CN 103569941 A 2/2014
CN 104377138 A 2/2015
(Continued)

*Primary Examiner* — Eduardo A Rodela
(74) *Attorney, Agent, or Firm* — Slater Matsil, LLP

(57) ABSTRACT

According to an embodiment, a sensor package includes an electrically insulating substrate including a cavity in the electrically insulating substrate, an ambient sensor, an integrated circuit die embedded in the electrically insulating substrate, and a plurality of conductive interconnect structures coupling the ambient sensor to the integrated circuit die. The ambient sensor is supported by the electrically insulating substrate and arranged adjacent the cavity.

21 Claims, 18 Drawing Sheets

Related U.S. Application Data division of application No. 15/086,573, filed on Mar. 31, 2016, now Pat. No. 10,186,468.

(51) Int. Cl.

| | | |
|---|---|---|
| *H01L 21/18* | (2006.01) | |
| *H01L 21/762* | (2006.01) | |
| *H01L 23/31* | (2006.01) | |
| *H01L 23/057* | (2006.01) | |
| *G01N 27/12* | (2006.01) | |
| *H01L 23/29* | (2006.01) | |
| *H01L 23/00* | (2006.01) | |
| *H01L 21/306* | (2006.01) | |
| *H01L 21/02* | (2006.01) | |
| *H01L 21/302* | (2006.01) | |
| *H01L 33/00* | (2010.01) | |
| *G01N 27/02* | (2006.01) | |
| *G01N 33/00* | (2006.01) | |
| *H01L 21/56* | (2006.01) | |
| *H01L 23/538* | (2006.01) | |
| *H05K 1/18* | (2006.01) | |

(52) U.S. Cl.
CPC ... *G01N 33/0036* (2013.01); *H01L 21/02016* (2013.01); *H01L 21/185* (2013.01); *H01L 21/187* (2013.01); *H01L 21/2007* (2013.01); *H01L 21/302* (2013.01); *H01L 21/306* (2013.01); *H01L 21/561* (2013.01); *H01L 21/7624* (2013.01); *H01L 21/76256* (2013.01); *H01L 23/057* (2013.01); *H01L 23/296* (2013.01); *H01L 23/31* (2013.01); *H01L 23/315* (2013.01); *H01L 23/3107* (2013.01); *H01L 23/3128* (2013.01); *H01L 23/3157* (2013.01); *H01L 23/5386* (2013.01); *H01L 24/19* (2013.01); *H01L 24/24* (2013.01); *H01L 24/96* (2013.01); *H01L 33/0093* (2020.05); *H05K 1/181* (2013.01); *H01L 21/568* (2013.01); *H01L 23/291* (2013.01); *H01L 23/295* (2013.01); *H01L 2224/04105* (2013.01); *H01L 2224/12105* (2013.01); *H01L 2224/24137* (2013.01); *H01L 2224/73267* (2013.01); *H01L 2924/14* (2013.01); *H01L 2924/1433* (2013.01); *H01L 2924/1461* (2013.01); *H01L 2924/1815* (2013.01); *H01L 2924/18162* (2013.01); *H01L 2924/3025* (2013.01)

(58) Field of Classification Search
CPC ... H01L 23/291; H01L 23/295; H01L 21/568; H01L 2224/04105; H01L 2224/12105; H01L 2224/24137; H01L 2224/73267; H01L 2924/14; H01L 2924/1433; H01L 2924/1461; H01L 2924/1815; H01L 2924/18162; H01L 2924/3025; H01L 23/49816; H01L 23/50; H01L 23/58; H01L 24/11; H01L 24/12; H01L 25/105; H01L 2924/15311; H01L 21/31; H01L 2224/73257; G01N 27/04; G01N 33/0009; G01N 27/128; G01N 27/028; G01N 33/0036; H05K 1/181; B81B 7/0032; B81B 7/0087; B81C 1/00261; B81C 1/0069

See application file for complete search history.

(56) References Cited

U.S. PATENT DOCUMENTS

| | | | |
|---|---|---|---|
| 6,867,471 | B2 | 3/2005 | Goller et al. |
| 7,943,423 | B2 | 5/2011 | Pohl et al. |
| 8,103,025 | B2 * | 1/2012 | Mullenborn ........... H04R 19/04 381/174 |
| 8,288,201 | B2 | 10/2012 | Pagaila et al. |
| 8,828,807 | B1 | 9/2014 | Wachter et al. |
| 8,872,288 | B2 | 10/2014 | Fuergut et al. |
| 8,901,739 | B2 | 12/2014 | Fuergut et al. |
| 8,907,476 | B2 | 12/2014 | Lin et al. |
| 9,099,454 | B2 | 8/2015 | Wachter et al. |
| 9,252,065 | B2 | 2/2016 | Lin et al. |
| 9,584,889 | B2 | 2/2017 | Escher-Poeppel et al. |
| 9,658,179 | B2 | 5/2017 | Rajaraman et al. |
| 9,698,105 | B2 | 7/2017 | Luan |
| 10,546,752 | B2 * | 1/2020 | Pindl ..................... H01L 23/053 |
| 2004/0041251 | A1 | 3/2004 | Goller et al. |
| 2006/0021881 | A1 | 2/2006 | Soundarrajan et al. |
| 2007/0107493 | A1 * | 5/2007 | Katsuda ............. G01N 33/0009 73/23.31 |
| 2007/0254411 | A1 | 11/2007 | Uhland et al. |
| 2008/0315334 | A1 | 12/2008 | Martin |
| 2009/0314095 | A1 | 12/2009 | Lu |
| 2011/0210439 | A1 | 9/2011 | Lim et al. |
| 2014/0346623 | A1 * | 11/2014 | Elian .................... H01L 24/97 257/417 |
| 2014/0374855 | A1 | 12/2014 | Lo |
| 2015/0014793 | A1 | 1/2015 | Yow et al. |
| 2015/0076636 | A1 | 3/2015 | Beer et al. |
| 2015/0166329 | A1 | 6/2015 | Cheng et al. |
| 2015/0226585 | A1 | 8/2015 | Yang |
| 2015/0287674 | A1 | 10/2015 | Schrank et al. |
| 2015/0323510 | A1 | 11/2015 | Huynh et al. |
| 2015/0377824 | A1 | 12/2015 | Ruhl et al. |
| 2016/0068387 | A1 * | 3/2016 | Nakanishi ............. B81C 1/0023 257/415 |
| 2016/0169758 | A1 * | 6/2016 | Hooper ................. B81B 7/0048 |

FOREIGN PATENT DOCUMENTS

| | | |
|---|---|---|
| KR | 20150024792 A | 3/2015 |
| KR | 20150059635 A | 6/2015 |

* cited by examiner

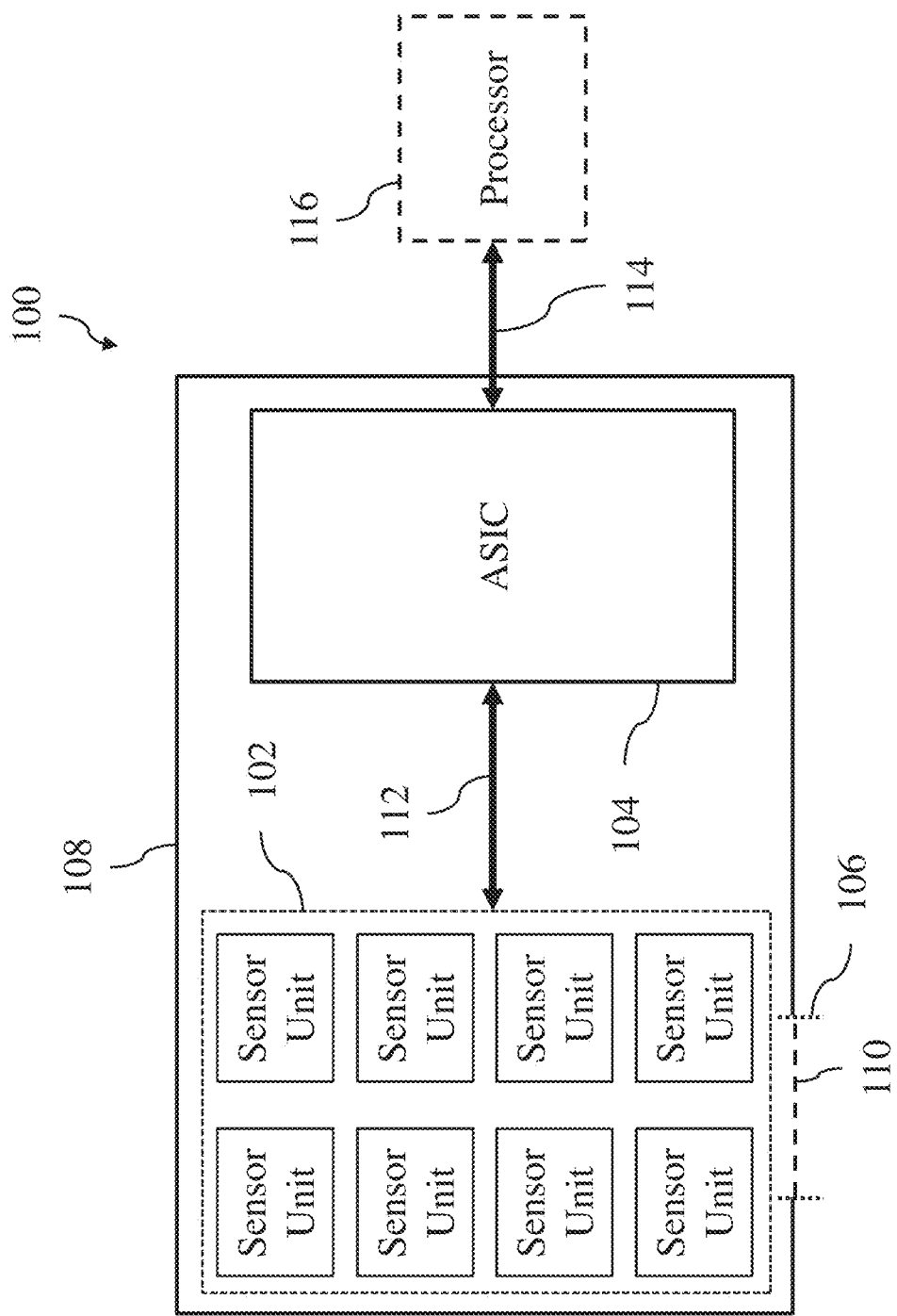

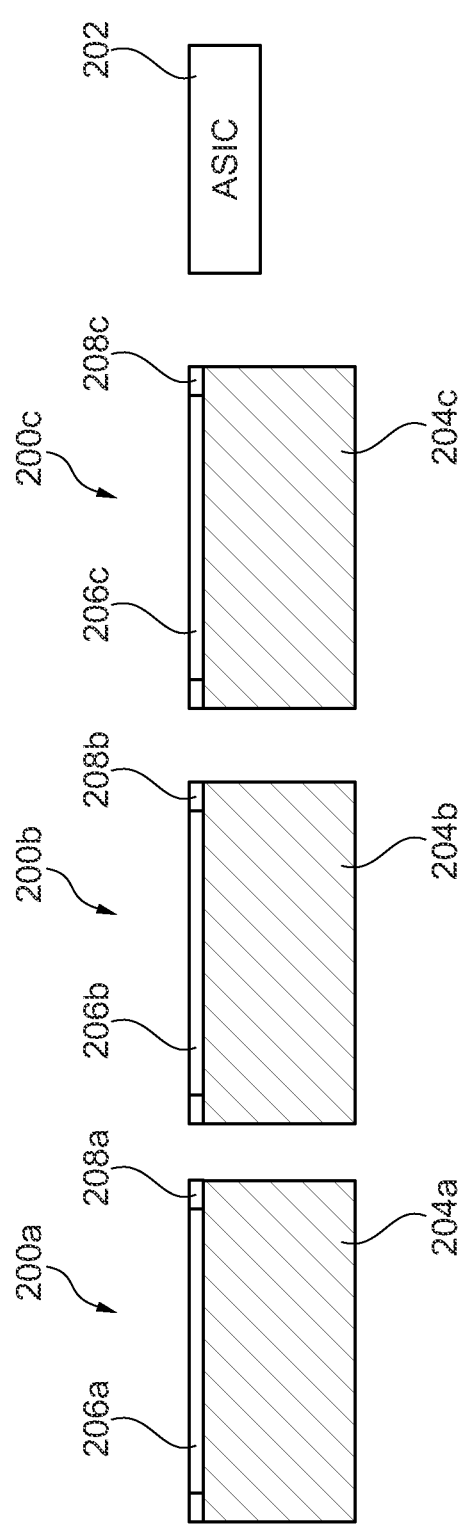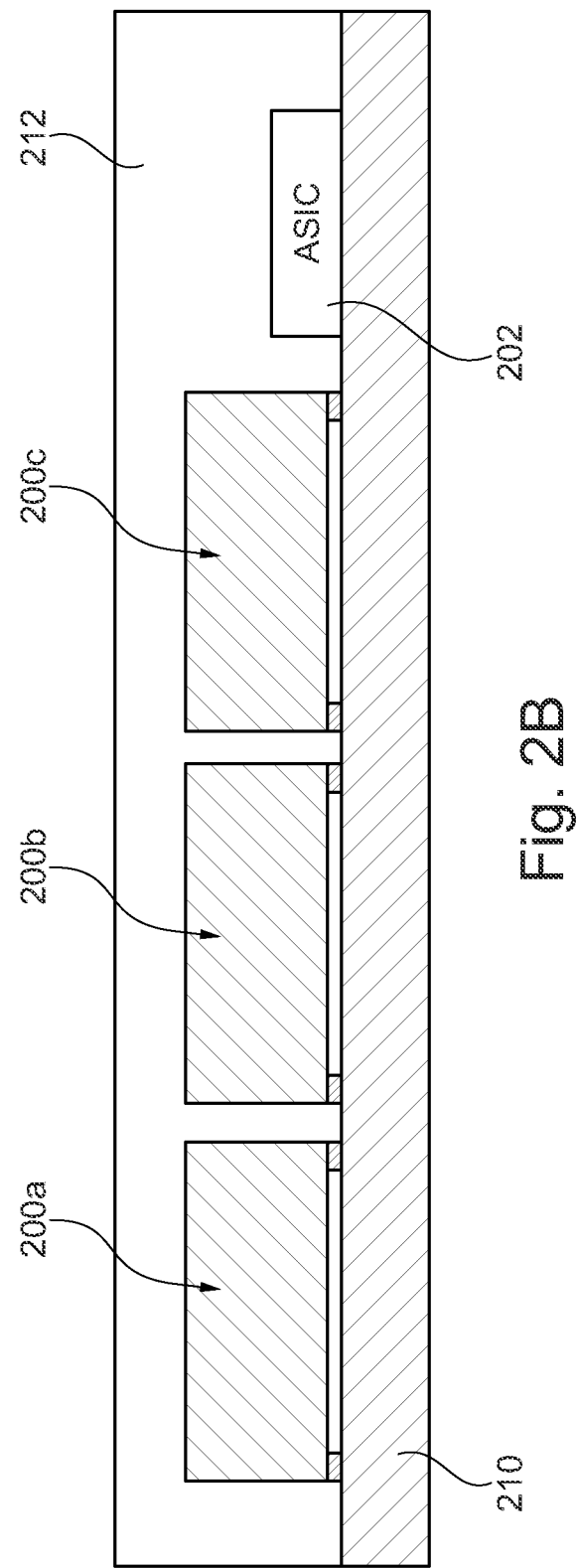

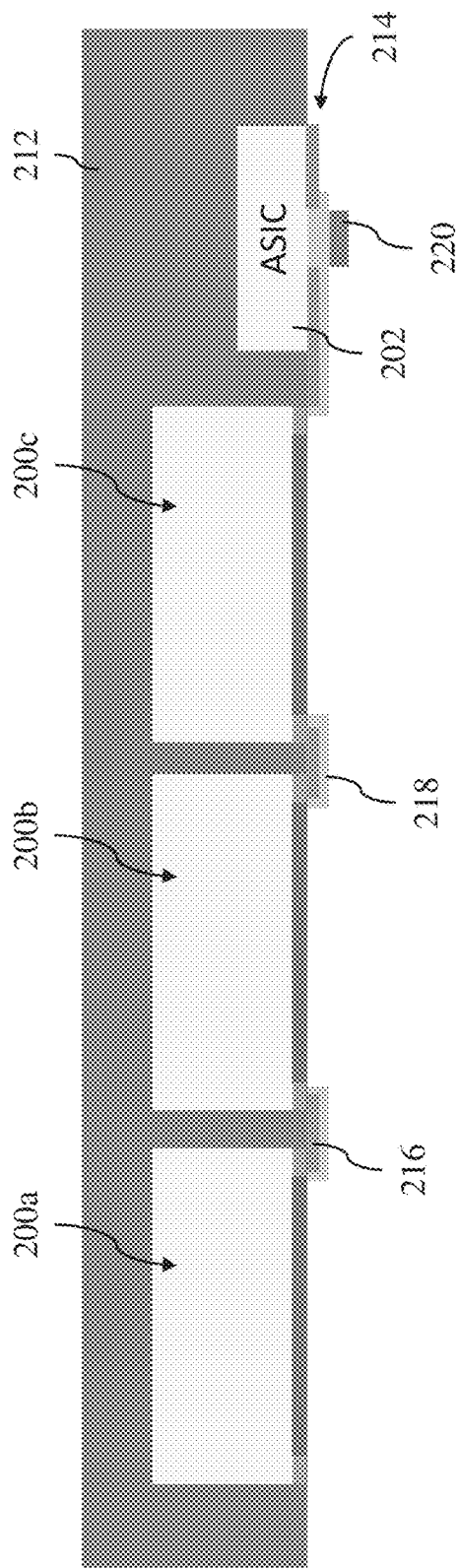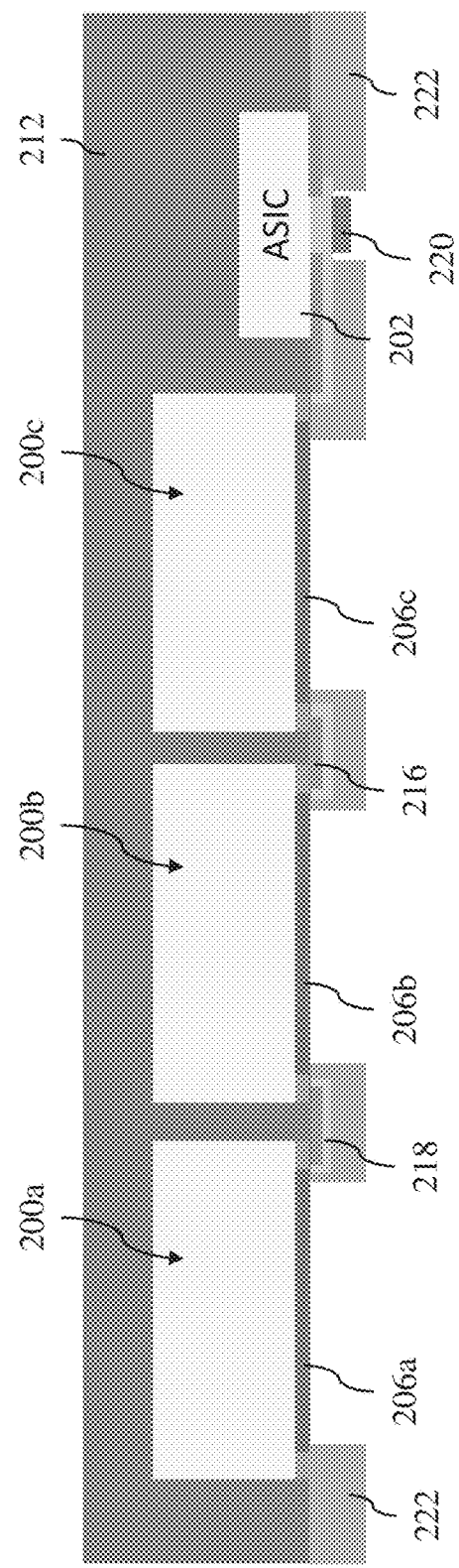

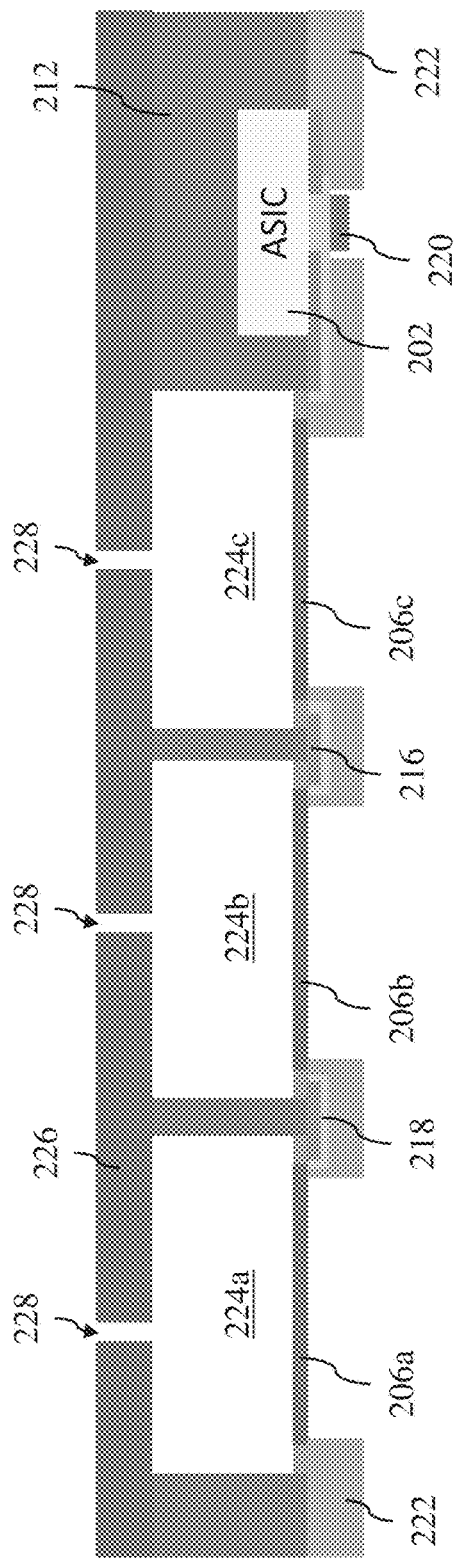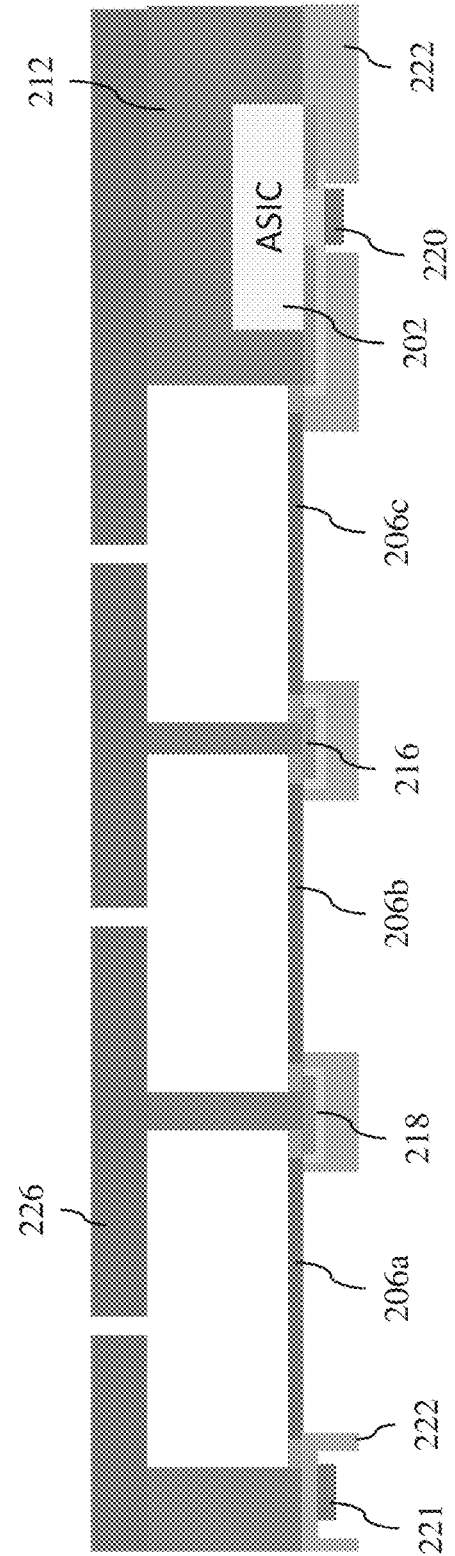
FIG 2G
FIG 2H

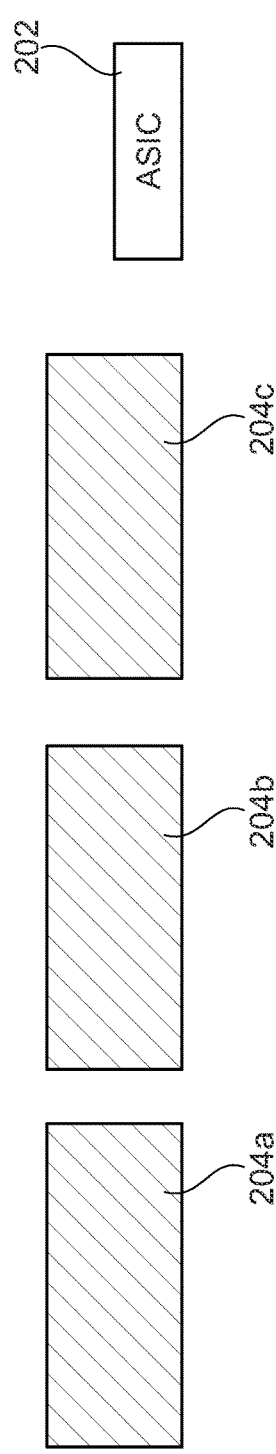
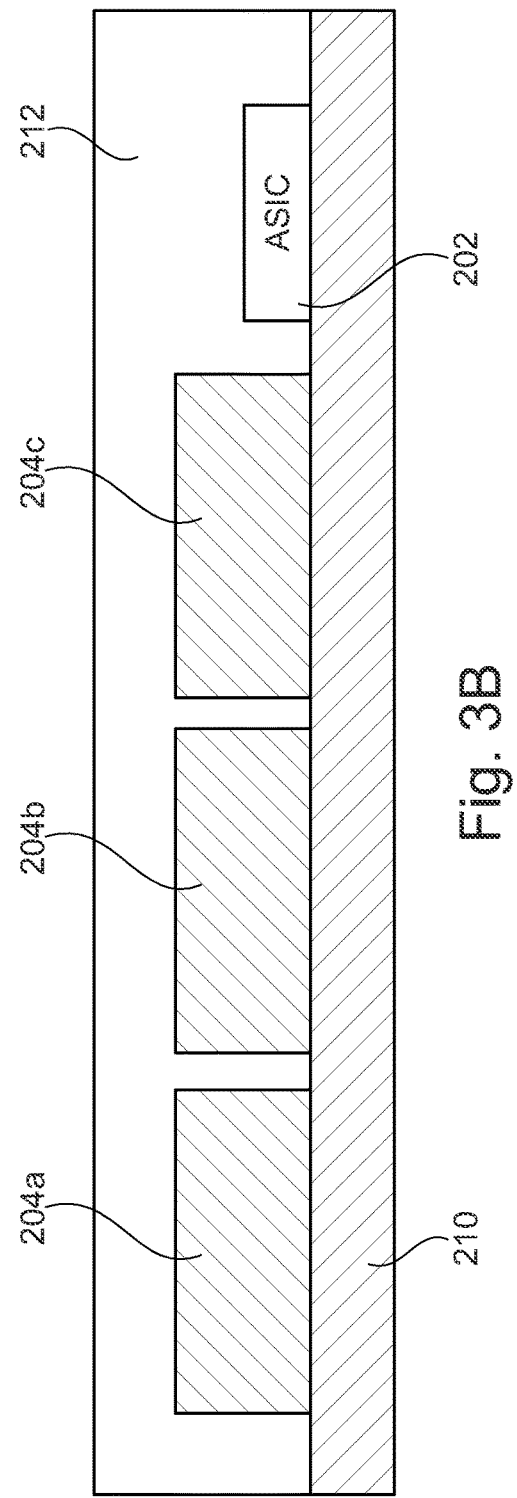

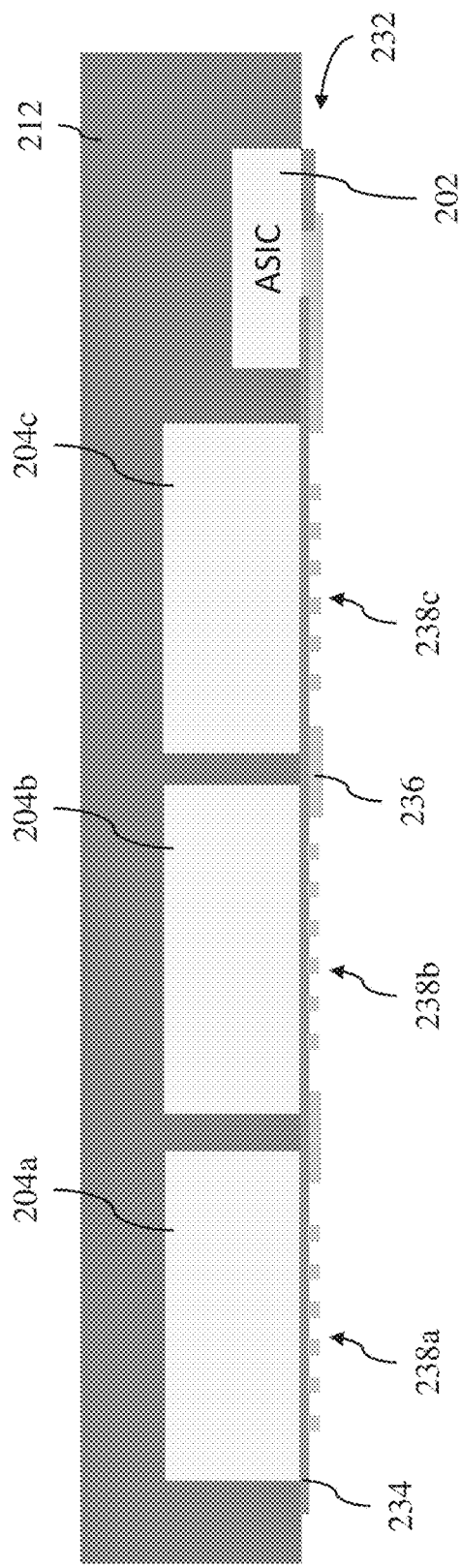
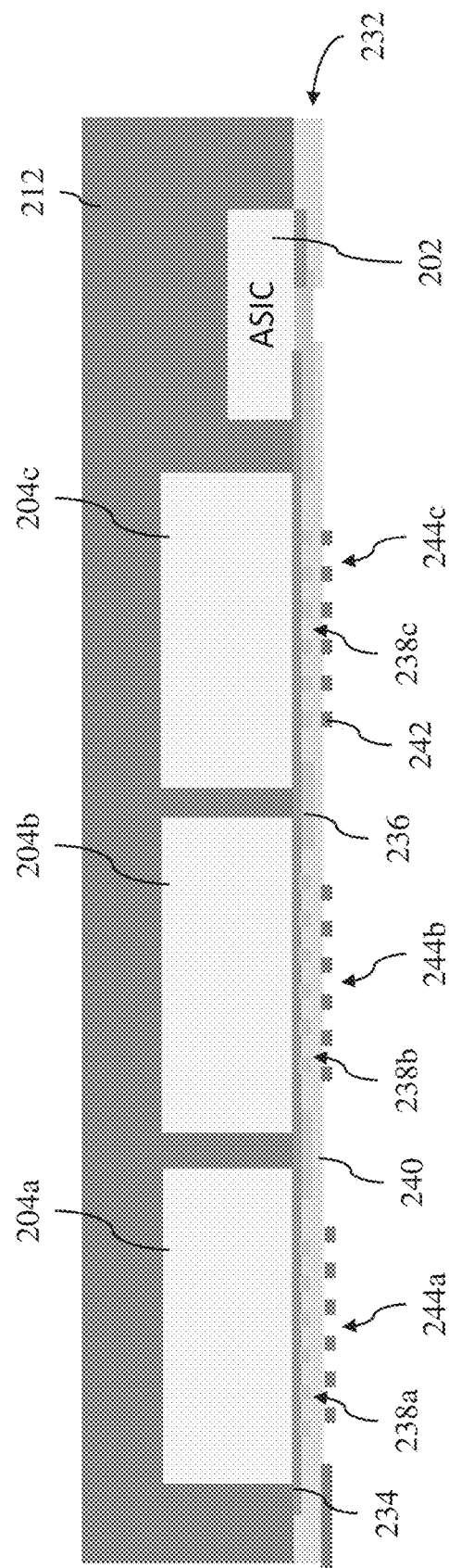
FIG 3C
FIG 3D

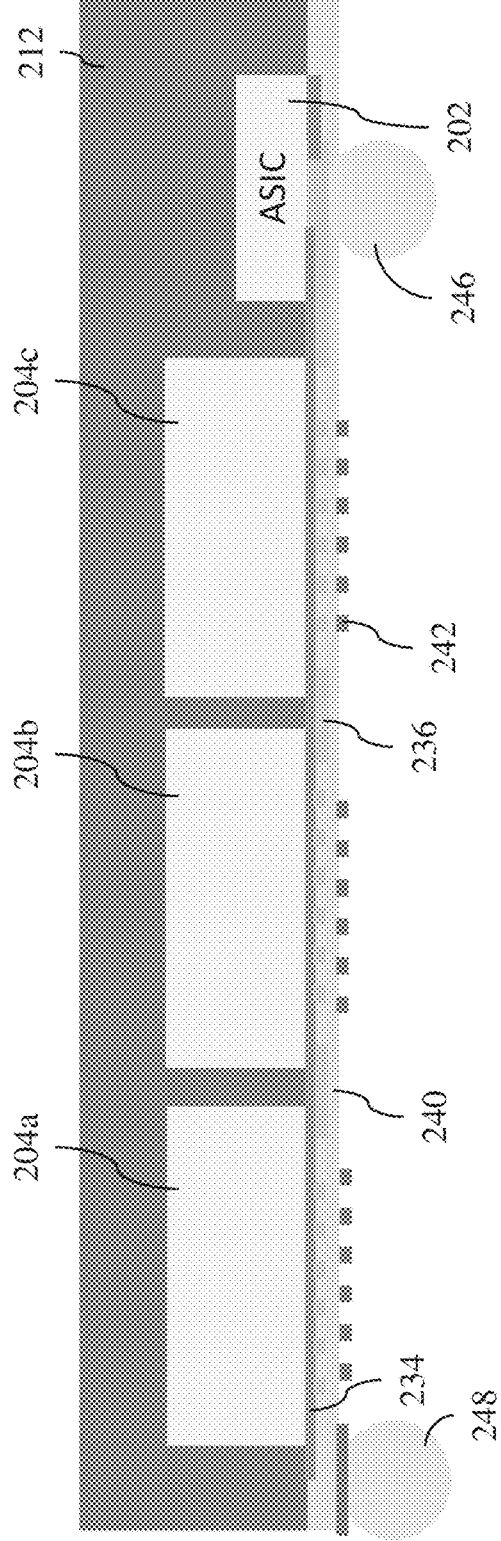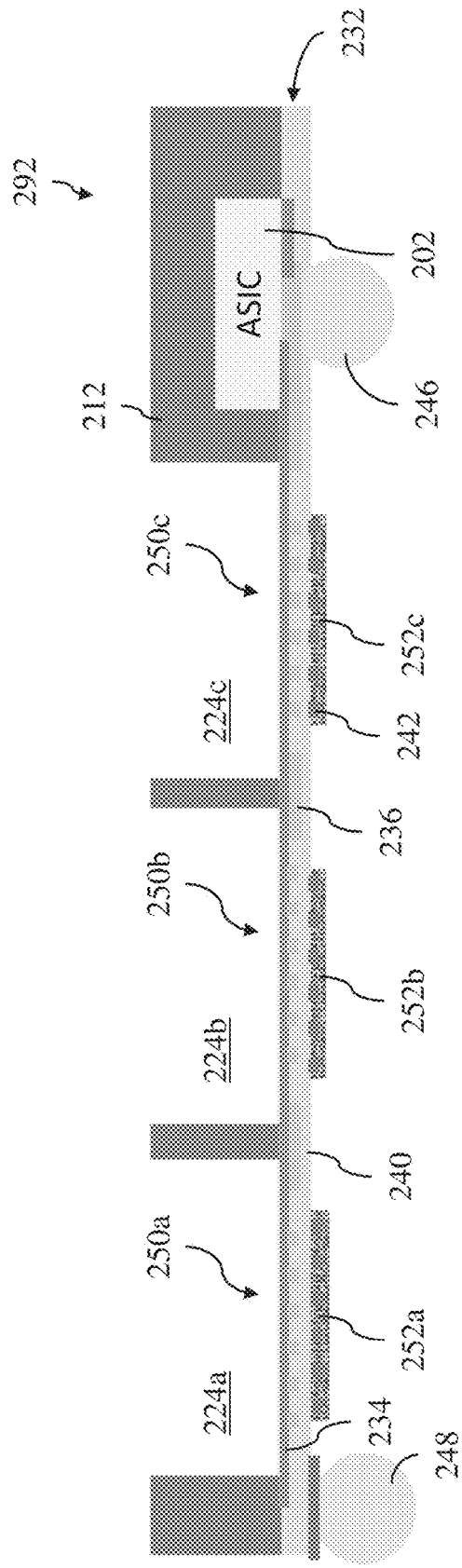

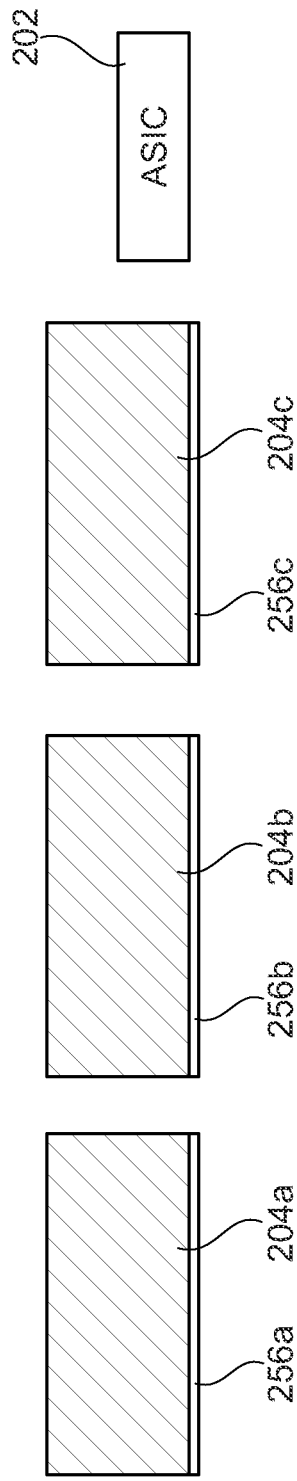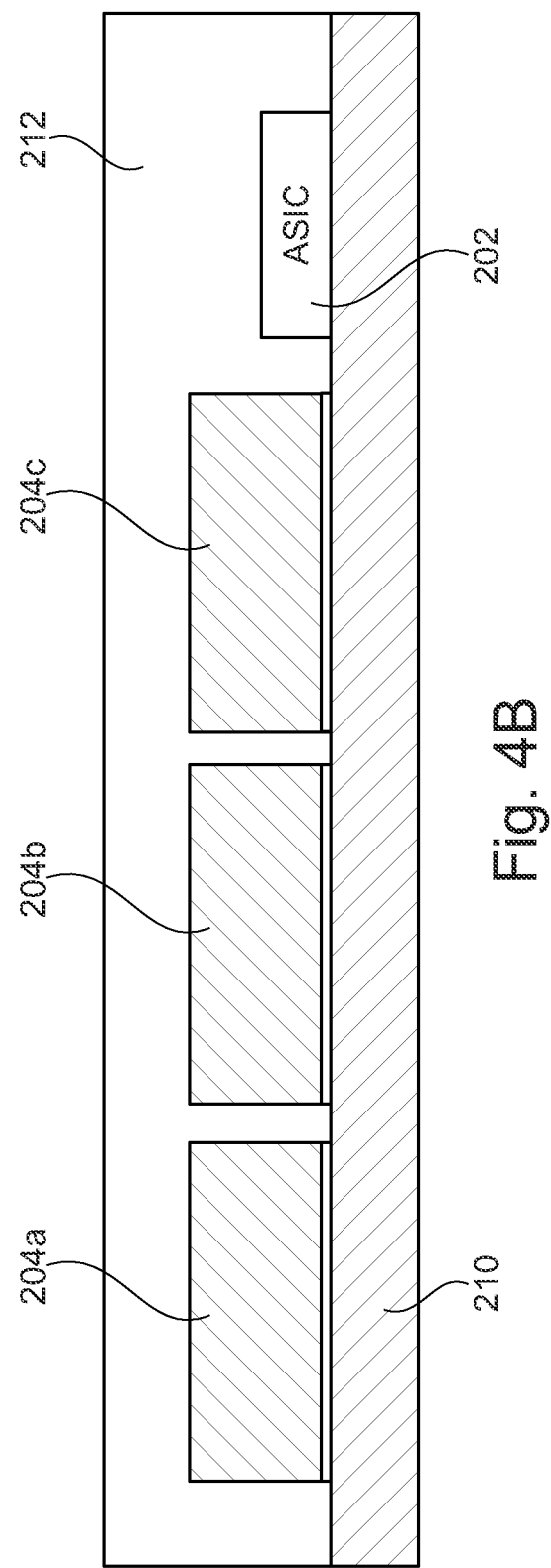

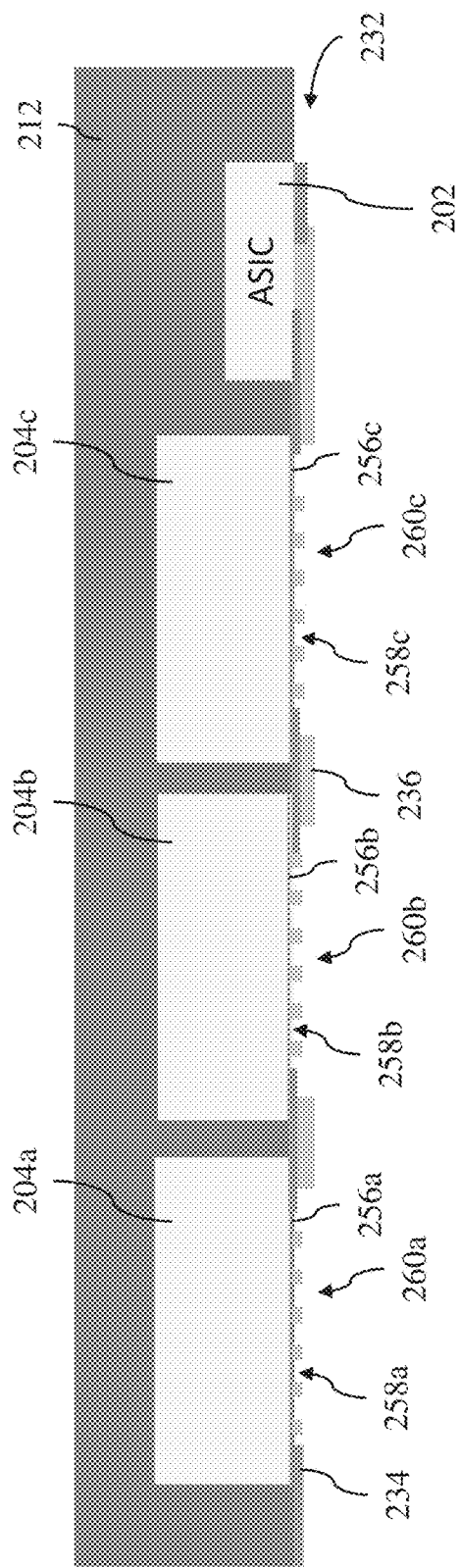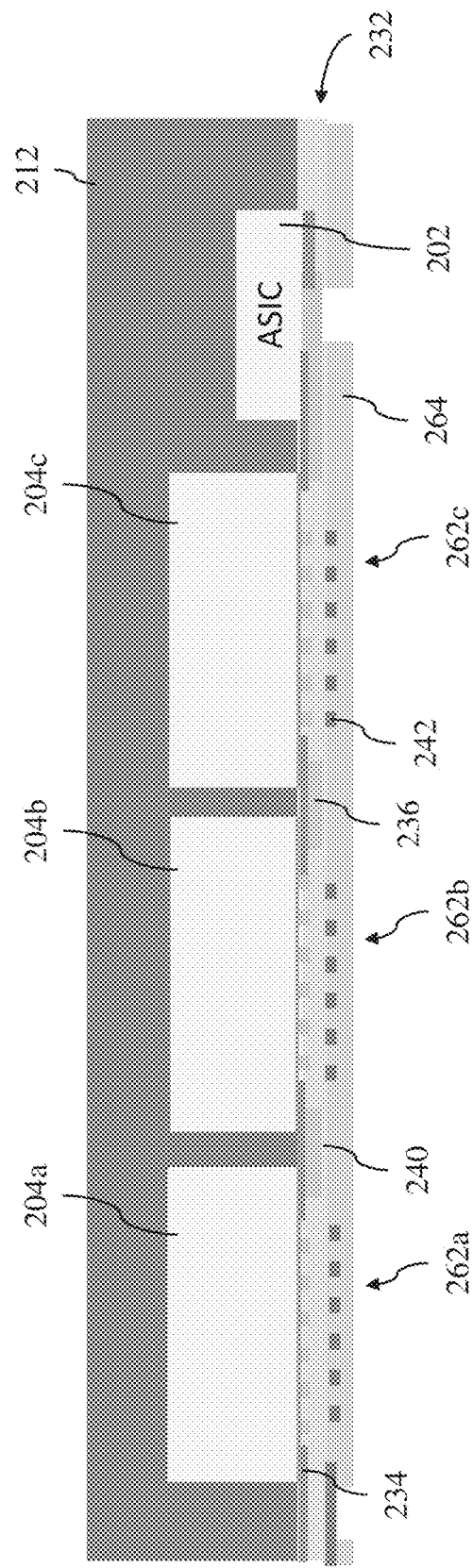

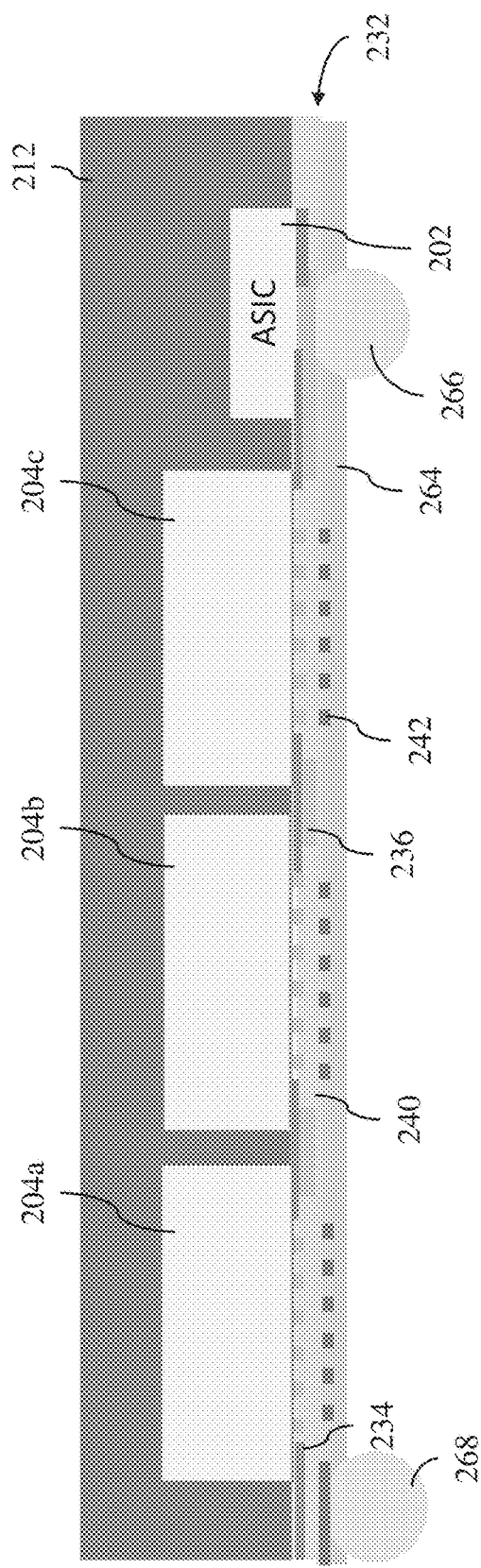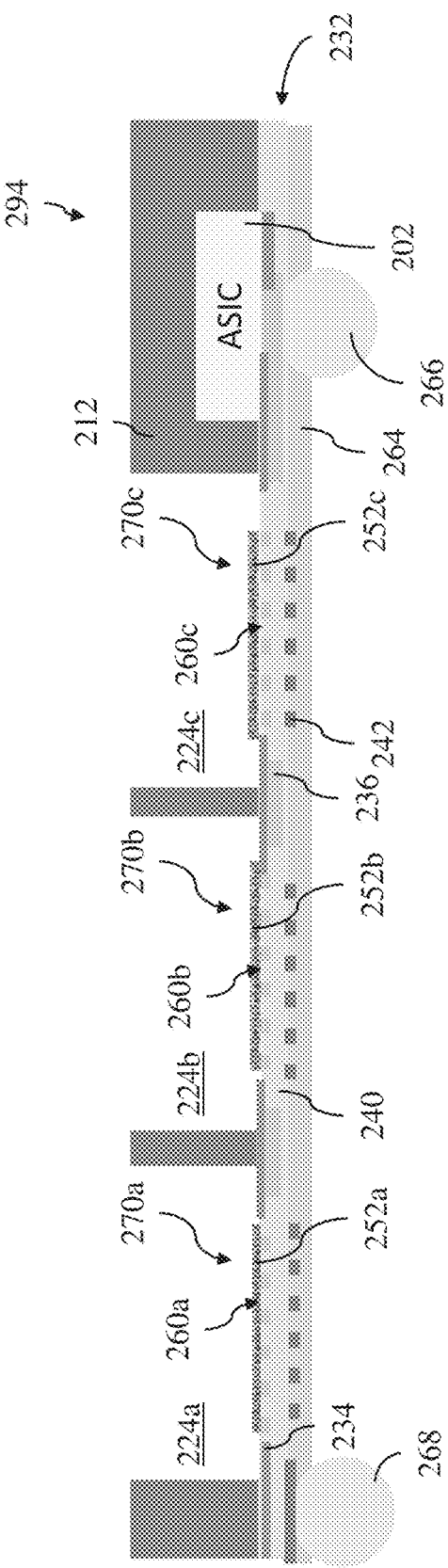

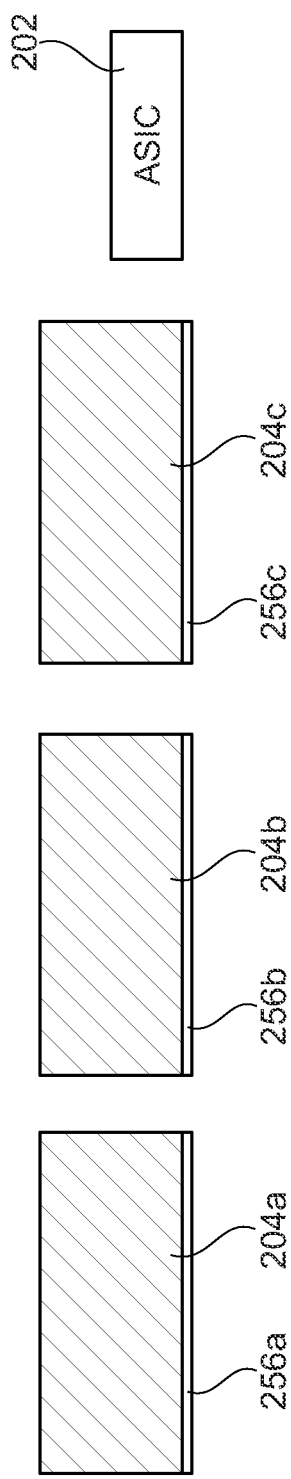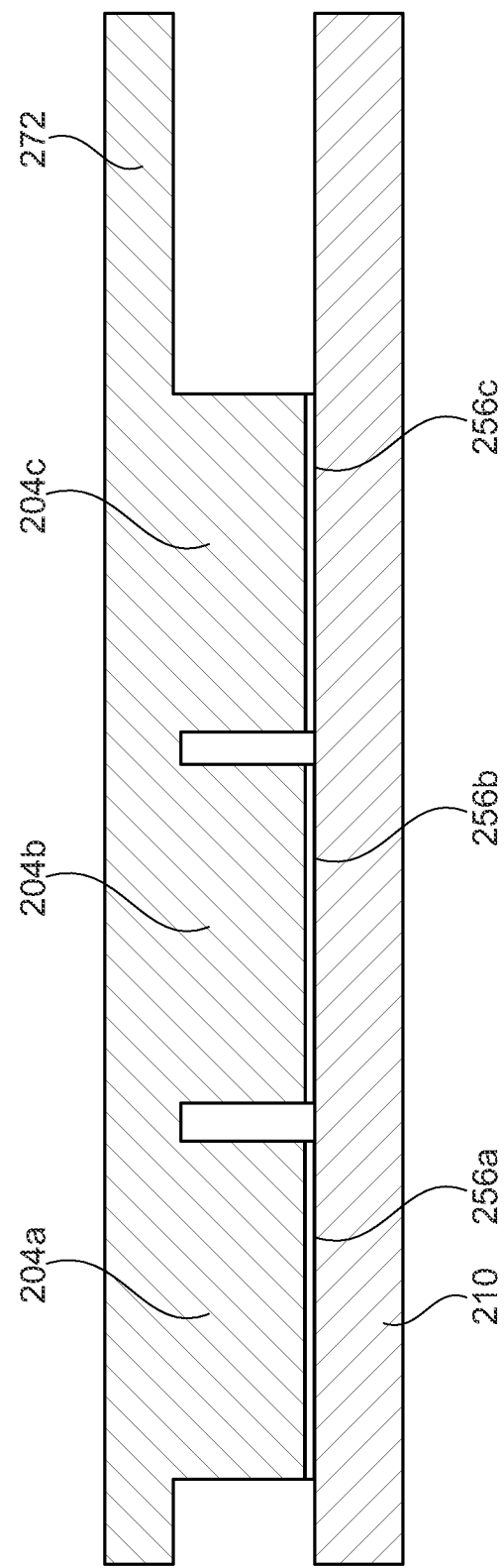

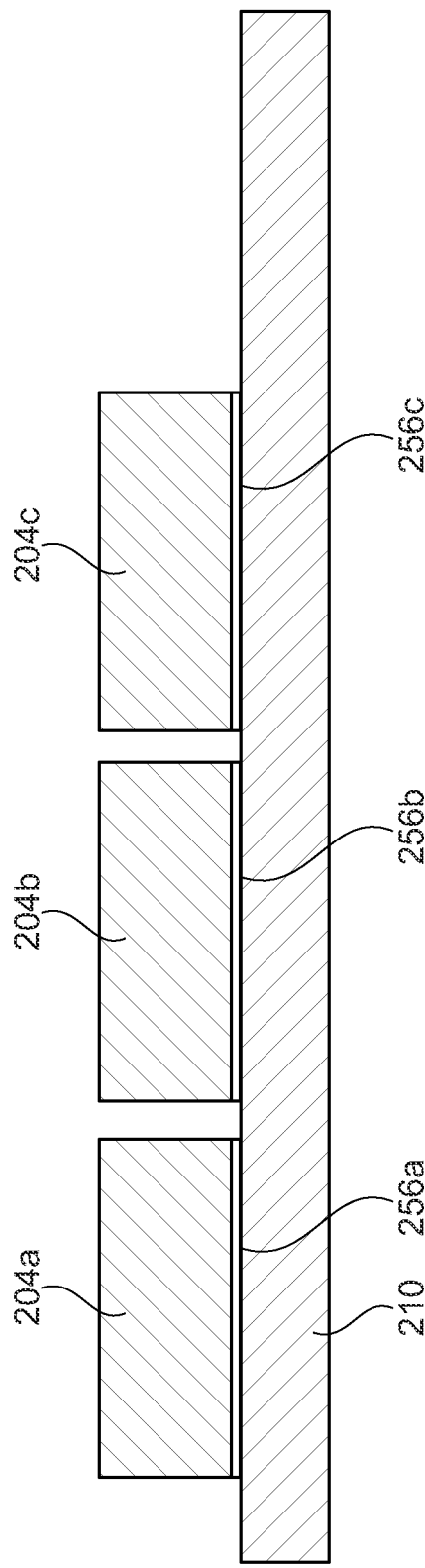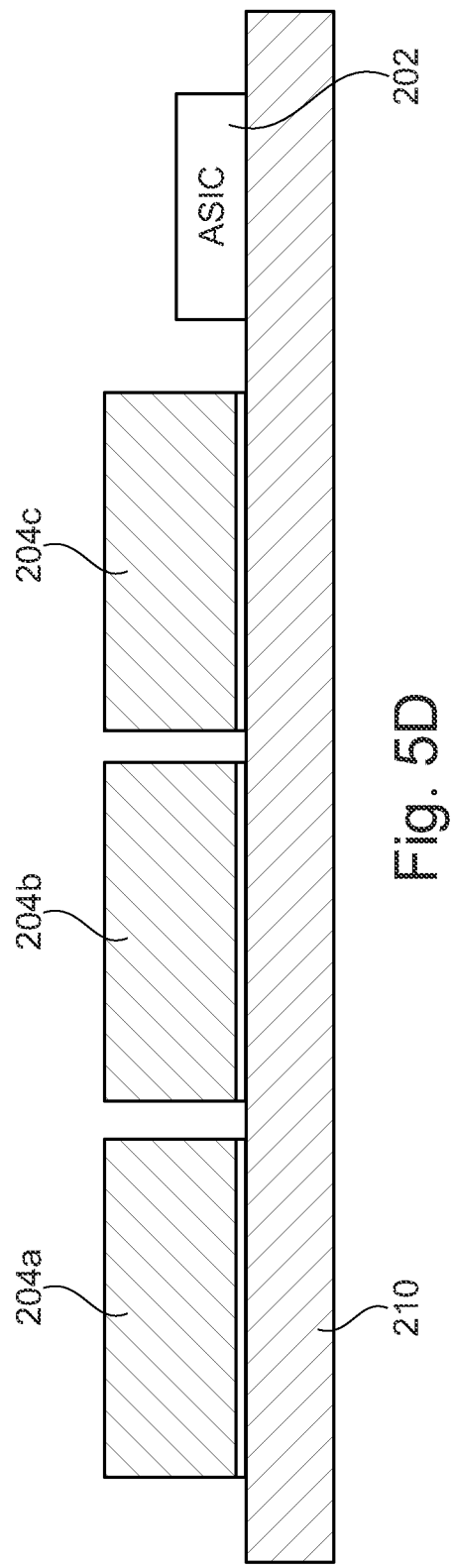

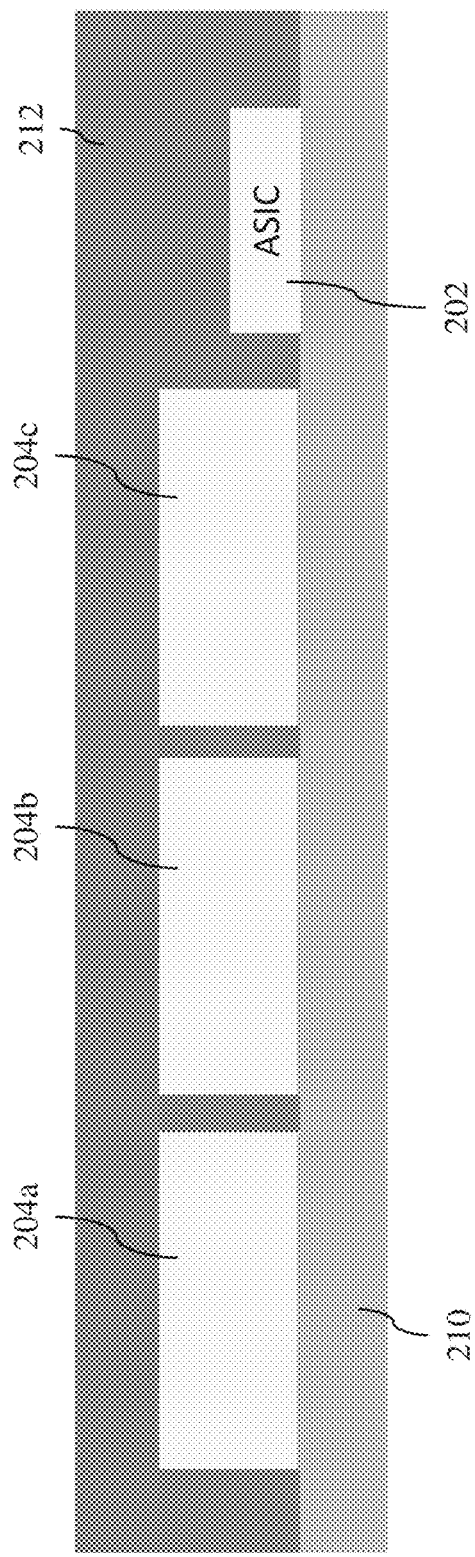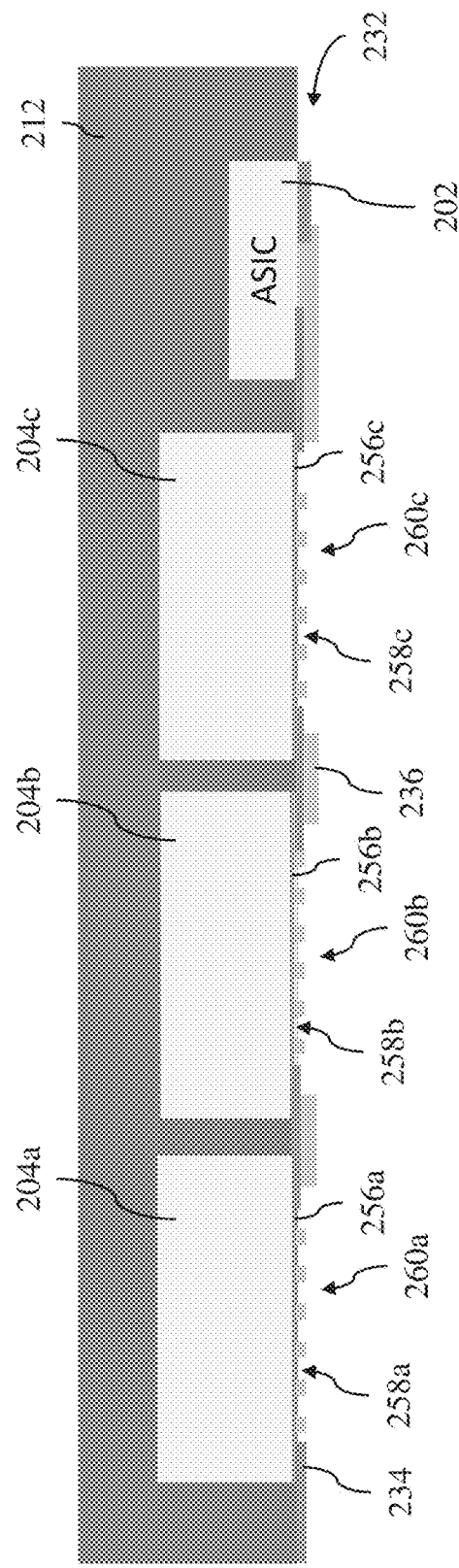
FIG 5E
FIG 5F

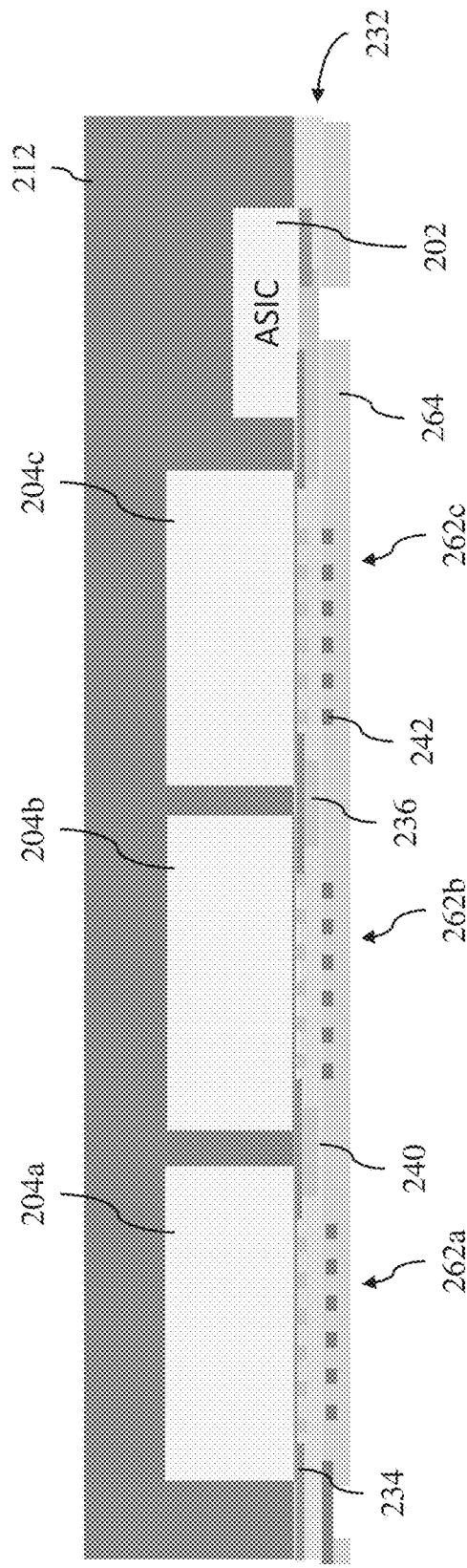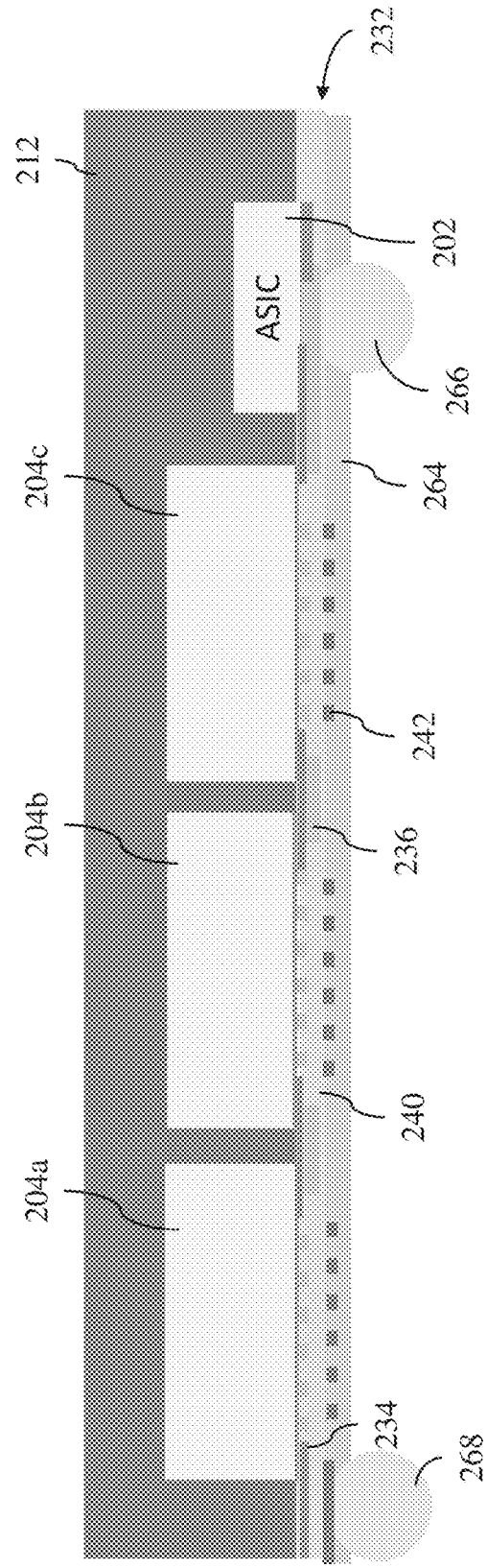

SYSTEM AND METHOD FOR A TRANSDUCER IN AN EWLB PACKAGE

This application is a divisional of U.S. patent application Ser. No. 16/227,761, filed on Dec. 20, 2018, which application is a divisional of Ser. No. 15/086,573, filed on Mar. 31, 2016, which applications are hereby incorporated herein by reference in their entirety.

TECHNICAL FIELD

The present invention relates generally to devices and packaging, and, in particular embodiments, to a system and method for an embedded wafer level ball grid array (eWLB) package.

BACKGROUND

Transducers that convert signals from one domain to another are often used in sensors. A common transducer used as a sensor is a pressure sensor that converts pressure differences and/or pressure changes to electrical signals. Pressure sensors have numerous applications including, for example, atmospheric pressure sensing, altitude sensing, and weather monitoring.

Microelectromechanical system (MEMS) based sensors include a family of transducers produced using micromachining techniques. MEMS, such as a MEMS pressure sensor, gather information from the environment by measuring the change of physical state in the transducer and transferring the signal to be processed by the electronics, which are connected to the MEMS sensor. MEMS devices may be manufactured using micromachining fabrication techniques similar to those used for integrated circuits.

MEMS devices may be designed to function as gas sensors, oscillators, resonators, accelerometers, gyroscopes, pressure sensors, microphones, and/or micro-mirrors, for example. Many MEMS devices use capacitive sensing techniques for transducing the physical phenomenon into electrical signals. In such applications, the capacitance change in the sensor is converted to a voltage or current signal using interface circuits. Other MEMS devices use resistive sensing techniques for transducing the physical phenomenon into electrical signals. In such applications, the resistive change in the sensor is converted to a voltage or current signal using interface circuits.

One type of example device is a gas sensor. Some gas sensors measure the resistance through a gas sensitive layer. For example, a humidity sensor may measure the resistance through a sensitive layer that absorbs water moisture from the air. As the water moisture is absorbed into the sensitive layer, the resistance of the layer is altered based on the humidity. Such humidity sensors may also include a heating element for use with the gas sensor.

For transducers that interact with an external environment, the device package may influence performance. For example, the device package may provide openings to the external environment and structural coupling or support to various sensing devices, such as a gas sensor, within the device package. The implementation of such structural supports or device packages provides opportunity for innovative implementations with expanded performance characteristics.

SUMMARY

According to an embodiment, a sensor package includes an electrically insulating substrate including a cavity in the electrically insulating substrate, an ambient sensor, an integrated circuit die embedded in the electrically insulating substrate, and a plurality of conductive interconnect structures coupling the ambient sensor to the integrated circuit die. The ambient sensor is supported by the electrically insulating substrate and arranged adjacent the cavity.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 illustrates a system block diagram of an embodiment packaged device;

FIGS. 2A, 2B, 2C, 2D, 2E, 2F, 2G, 2H, and 2I illustrate cross-sectional views of processing stages for an embodiment packaged device;

FIGS. 3A, 3B, 3C, 3D, 3E, and 3F illustrate cross-sectional views of processing stages for an embodiment packaged device;

FIGS. 4A, 4B, 4C, 4D, 4E, and 4F illustrate cross-sectional views of processing stages for an embodiment packaged device;

FIGS. 5A, 5B, 5C, 5D, 5E, 5F, 5G, 5H, and 5I illustrate cross-sectional views of processing stages for an embodiment packaged device;

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

Figure 2E:
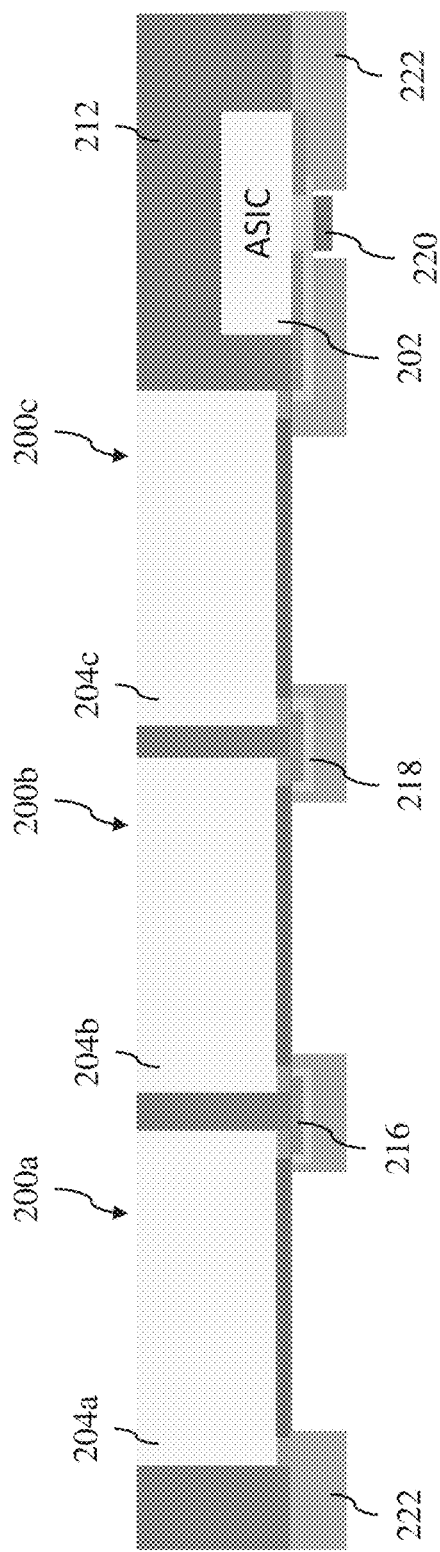

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Description is made with respect to various embodiments in a specific context, namely gas sensors, and more particularly, MEMS gas sensors in an embedded wafer level ball grid array (eWLB). Some of the various embodiments described herein include eWLB packaging, gas sensors, MEMS gas sensors, embedded heating elements, silicon free eWLB substrate packages, and MEMS gas sensors without silicon substrates in eWLB packages. In other embodiments, aspects may also be applied to other applications involving any type of sensor or transducer with any type of device package according to any fashion as known in the art.

In various embodiments, a gas sensor includes a heating element. For example, the heating element may be used to reset the gas sensor, such as by evaporating absorbed gases, or may be used in order to increase the sensing speed of the gas sensors. In such embodiments, the time period for sensing the concentration of a certain gas using a sensitive material may be decreased when the sensitive material is heated using the heating element. For various gas sensors, a semiconductor substrate, such as a silicon substrate, near the heating element may operate as a heat sink for the heating element. Such a structure may lead to wasted energy or limited performance. Thus, according to various embodiments, gas sensors are formed or arranged in a package without a semiconductor substrate.

According to various embodiments, one or more MEMS gas sensors are packaged in an eWLB package having cavities formed directly in the molding compound of the eWLB package. The one or more MEMS gas sensors are formed next to the cavities. In such embodiments, the MEMS gas sensors are not attached to semiconductor substrates, which include cavities in the substrates, but are instead supported by the molding compound of the eWLB package, which includes the cavities adjacent or contacting the MEMS gas sensor. In some such embodiments, the MEMS gas sensor without a semiconductor substrate near the gas sensitive layer and the heating element may include improved performance characteristics due to the reduced thermal capacity of the packaged device.

FIG. 1 illustrates a system block diagram of an embodiment packaged device 100 including MEMS sensor 102, application specific integrated circuit (ASIC) 104, and package 108. According to various embodiments, MEMS sensor 102 includes one or more MEMS sensor units. In particular embodiments, MEMS sensor 102 includes multiple ambient sensors, such as eight ambient sensor units as shown for example. In some embodiments, the ambient sensor units of MEMS sensor 102 are gas sensors. In alternative embodiments, the ambient sensor units of MEMS sensor 102 are altitude or pressure sensors, for example. MEMS sensor 102 electrically communicates with ASIC 104 through electrical interface 112. Further, MEMS sensor 102 is in fluid communication with the ambient environment through opening 106 in package 108.

According to various embodiments, package 108 is a wafer that supports and includes MEMS sensor 102 and ASIC 104. In particular embodiments, package 108 is an embedded wafer that may be formed by an embedding process applied to MEMS sensor 102 and ASIC 104. In such embodiments, package 108 may be formed as an eWLB package including MEMS sensor 102 and ASIC 104. Thus, package 108 may include embedding material that surrounds MEMS sensor 102 and ASIC 104 while simultaneously providing opening 106 for fluid communication between MEMS sensor 102 and the ambient environment.

According to various embodiments, opening 106 is depicted schematically and may include multiple openings arranged throughout package 108 in relation to MEMS sensor 102 and, in particular, may include openings for each sensor unit within MEMS sensor 102. Further, opening 106 includes membrane no in some embodiments. Membrane no is gas permeable and liquid impermeable in some embodiments. Thus, packaged device 100 may be referred to as waterproof in some embodiments. For example, in specific embodiments, membrane no includes a hydrophobic structure that is gas permeable. The structure of membrane no may also be oleophobic or lipophobic. Thus, in various embodiments, membrane no may allow gases to pass through opening 106 while preventing or limiting liquids from passing through opening 106. In alternative embodiments, membrane no is omitted.

In various embodiments, as gases, such as water vapor, carbon monoxide, or carbon dioxide for example, pass through opening 106, MEMS sensor 102 may sense the concentration of these gases. In particular embodiments, MEMS sensor 102 includes different sensor units for different gas types, such as water vapor, carbon monoxide, and carbon dioxide, for example. The sensor units for different gas types may be implemented with different functional elements that are sensitive to different specific gases. For example, in embodiments including eight sensor units in MEMS sensor 102, MEMS sensor 102 may be sensitive to eight different gases for sensing the concentration of each of the eight different gases at the eight sensor units, respectively. In various embodiments, the sensor units may be sensitive to more than one type of gas. In particular embodiments, the different sensor units may each be sensitive to multiple gases, where the sum of the sensor unit signals is different for different gases. In such embodiments, by monitoring the combined outputs of the different sensor units in MEMS sensor 102, the concentration of a specific gas or a group of different gases may be determined, such as by using principle component analysis, for example. According to various embodiments, MEMS sensor 102 may be a single die with multiple sensor units or MEMS sensor 102 may be multiple dies, each including one or more sensor units.

According to various embodiments, sensed signals generated by the one or more sensor units of MEMS sensor 102 are communicated to ASIC 104 through electrical interface 112. In such embodiments, the sensed signals may be analog electrical signals generated by the one or more sensor units of MEMS sensor 102. ASIC 104 receives the sensed signals and provides the sensed signals through external interface 114 to processor 116, which is an optional external element to package 108. In various embodiments, ASIC 104 includes a buffer or amplifier, an analog-to-digital converter, or a bus interface circuit. In such embodiments, ASIC 104 may buffer or amplify the sensed signals, convert the sensed signals to digital signals, or provide the signals through external interface 114 using an interface protocol, such as a bus protocol. ASIC 104 may also receive control information through external interface 114, such as initialization commands for a calibration or characterization sequence.

In various embodiments, ASIC 104 is a separate semiconductor die from MEMS sensor 102, which may include multiple sensor units as separate dies. Processor 116 may be a separate unit from package 108 connected to a same system. For example, processor 116 may be attached to a same printed circuit board (PCB) as package 108 in a mobile computing unit, such as a smartphone, smartwatch, tablet computer, or laptop computer, for example. In some embodiments, processor 116 is a digital signal processor (DSP). In other embodiments, processor 116 is a general purpose processor, such as a microprocessor. In still further embodiments, processor 116 is a field programmable gate array (FPGA).

Further description of different embodiment packaged devices is provided hereinafter. Such description applies to different embodiment implementations of packaged device 100 with MEMS sensor 102 and ASIC 104.

FIGS. 2A, 2B, 2C, 2D, 2E, 2F, 2G, 2H, and 2I illustrate cross-sectional views of processing stages or steps for a fabrication sequence of an embodiment packaged device. FIG. 2A illustrates a processing stage or step including gas sensor chips 200a, 200b, and 200c and ASIC 202. According to various embodiments, gas sensor chip 200a includes substrate 204a, gas sensing region 206a, and border region 208a; gas sensor chip 200b includes substrate 204b, gas sensing region 206b, and border region 208b; and gas sensor chip 200c includes substrate 204c, gas sensing region 206c, and border region 208c.

According to various embodiments, any number of gas sensor chips may be included. As shown, three gas sensor chips, gas sensor chips 200a, 200b, and 200c, are included in the structure of FIG. 2A, and, consequently, in the packaged device. In other embodiments, only a single gas sensor chip, gas sensor chip 200a, is included. In further embodiments, only two gas sensor chips, gas sensor chips 200a and 200b, are included. In some embodiments, more than three gas sensor chips are included, such as from eight to sixteen gas sensor chips. In various embodiments, any number of gas sensor chips may be included, such as tens, hundreds, or even thousands of gas sensor chips.

In various embodiments, substrates 204a, 204b, and 204c may be semiconductor substrates. In a specific example embodiment, substrates 204a, 204b, and 204c are silicon substrates. In other embodiments, substrates 204a, 204b, and 204c are formed of other semiconductor materials, such as carbon or germanium, or semiconductor compound materials, such as gallium arsenide, indium phosphide, silicon germanium, or silicon carbide, for example. In alternative embodiments, substrates 204a, 204b, and 204c are formed of non-semiconducting materials, such as polymer based materials or metals. For example, substrates 204a, 204b, and 204c may be formed of a structurable photoresist, glass, copper, or aluminum in various different embodiments.

Gas sensing regions 206a, 206b, and 206c are formed on top of substrates 204a, 204b, and 204c. In such embodiments, gas sensing regions 206a, 206b, and 206c include active gas sensitive layers. Further, border regions 208a, 208b, and 208c may surround gas sensing regions 206a, 206b, and 206c and include inactive layers. Further details of various gas sensor implementations for gas sensing regions 206a, 206b, and 206c may be found in U.S. application Ser. No. 14/751,660, filed on Jun. 26, 2015 and entitled "Graphene Gas Sensor for Measuring the Concentration of Carbon Dioxide in Gas Environments," and U.S. application Ser. No. 14/749,102, filed on Jun. 24, 2015 and entitled "System and Method for a MEMS Transducer," which are both incorporated herein by reference in their entirety.

In various embodiments, ASIC 202 is included as a separate semiconductor die in FIG. 2A. ASIC 202 may be implemented as described hereinabove in reference to ASIC 104 in FIG. 1 and further description is not provided herein.

FIG. 2B illustrates a processing stage or step including carrier substrate 210, embedding material 212, gas sensor chips 200a, 200b, and 200c, and ASIC 202. According to various embodiments, gas sensor chips 200a, 200b, and 200c and ASIC 202 are flipped over and placed on carrier substrate 210. In such embodiments, gas sensor chips 200a, 200b, and 200c and ASIC 202 may be placed on carrier substrate 210 using pick and place techniques, such as by using a surface mount technology (SMT) component placement system. Once gas sensor chips 200a, 200b, and 200c and ASIC 202 are arranged on carrier substrate 210, embedding material 212 is formed around and embeds gas sensor chips 200a, 200b, and 200c and ASIC 202.

In various embodiments, embedding material 212 is formed in an embedding process. For example, embedding material 212 may be deposited according to an embedded wafer level ball grid array (eWLB) process. In such embodiments, embedding material 212 may be deposited using injection molding. In further embodiments, embedding material 212 may be deposited using embedding granules applied to the surface of carrier substrate 210 and melted to form embedding material 212. In other embodiments, embedding material 212 may be deposited as a liquid embedding material.

According to various embodiments, embedding material 212 includes an electrically insulating material. In some embodiments, embedding material 212 is a polymer. In further embodiments, embedding material 212 is selected from a group of materials including epoxy resins, laminates, and plastics. In other embodiments, embedding material 212 is glass, such as a silicate glass or the like. For example, embedding material 212 is one of borosilicate glass, phosphosilicate glass, or borophosphosilicate glass. In still other embodiments, embedding material 212 is a ceramic or a polymer molding material with ceramic particles. In various embodiments, embedding material 212 is any electrically insulating encasing or embedding material.

In various embodiments, carrier substrate 210 is a temporary substrate, such as a wafer or chip. In such embodiments, carrier substrate 210 may be formed of a structural material. For example, carrier substrate 210 is formed of semiconductor, metal, glass, or polymer materials in different embodiments. Specifically, carrier substrate 210 may be a plastic in some embodiments or glass, such as silicon oxide, in other embodiments.

FIG. 2C illustrates a processing stage or step including redistribution layer (RDL) 214 formed on embedding material 212 and coupling gas sensor chips 200a, 200b, and 200c, and ASIC 202. Following forming of embedding material 212, carrier substrate 210 is removed and RDL 214 is formed to couple gas sensor chips 200a, 200b, or 200c, or ASIC 202 together. In such embodiments, RDL 214 includes isolation layer 216 and conductive layer 218. In such embodiments, conductive layer 218 is formed between points of electrical contact on gas sensor chips 200a, 200b, or 200c, or ASIC 202. The various conductive traces of conductive layer 218 are electrically isolated from each other and from unintended contact points by isolation layer 216, which is electrically insulating.

In various embodiments, isolation layer 216 is a dielectric material, such as an oxide, a nitride, or a polymer. In a specific embodiment, isolation layer 216 is polyimide. In some embodiments, conductive layer 218 is a metal, such as aluminum, copper, titanium, nickel, or gold. In alternative embodiments, conductive layer 218 is a conductive non-metal, such as a doped semiconductor or conductive polymer.

Further embodiments may include contact pad 220. Any number of contact pads, such as contact pad 220, may be formed throughout the structure to form electrical contacts to gas sensor chips 200a, 200b, or 200c, or ASIC 202, for example. In various embodiments, contact pad 220 may be formed as an additional layer of metal, such as aluminum, copper, titanium, nickel, or gold. In other embodiments, contact pad 220 may be formed of a metal silicide using a silicide process. In still further embodiments, contact pad 220 is formed of solder.

FIG. 2D illustrates a processing stage or step including the structure of FIG. 2C with the addition of structural material 222. According to various embodiments, structural material 222 may be formed and patterned on the structure to leave gas sensing regions 206a, 206b, and 206c exposed and provide structural support for a finished package. In such embodiments, structural material 222 is a glass, such as silicon dioxide, or a polymer based material. In other embodiments, structural material 222 is omitted.

FIG. 2E illustrates a processing stage or step including the structure of FIG. 2D after embedding material 212 has been thinned from the topside (in relation to the illustrated figure). The thinning process exposes substrates 204a, 204b, and 204c of gas sensor chips 200a, 200b, and 200c, respectively.

In various embodiments, embedding material 212 is removed using a wafer thinning process, such as by grinding using an abrasive or using a chemical mechanical polish (CMP).

Figure 2F:
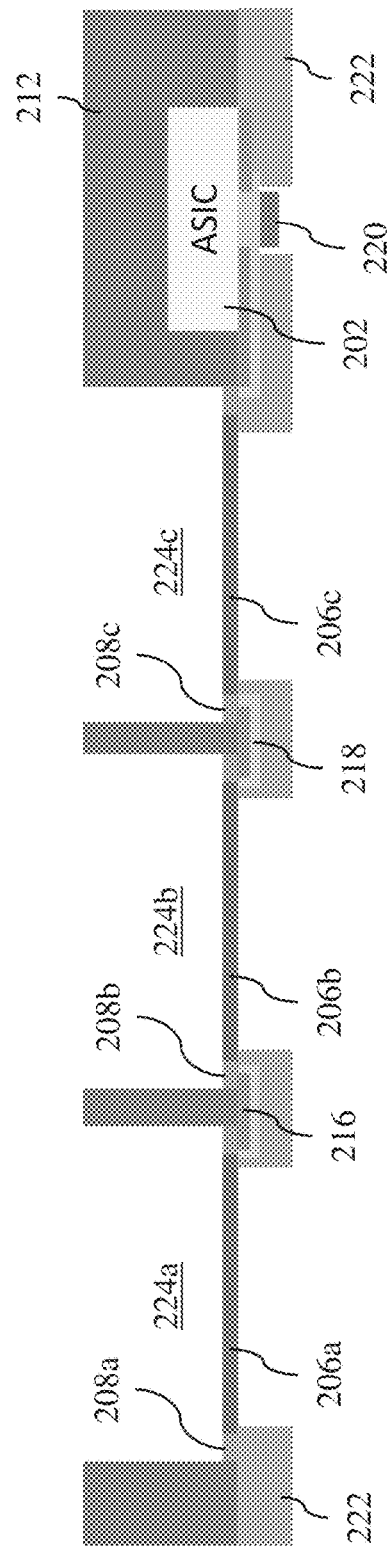

FIG. 2F illustrates a processing stage or step including the structure of FIG. 2E after a selective etch has been applied to remove substrates 204a, 204b, and 204c and form cavities 224a, 224b, and 224c. According to various embodiments, substrates 204a, 204b, and 204c are removed using a wet etch process or a plasma etch process. In such embodiments, the etch process may be a selective etch for selectively etching the material of substrates 204a, 204b, and 204c. In various embodiments, additional protection or masking layers, such as including a photoresist material, may be formed on the structure (not shown) while leaving substrates 204a, 204b, and 204c exposed to the etchant.

After removing substrates 204a, 204b, and 204c and forming cavities 224a, 224b, and 224c, gas sensing regions 206a, 206b, and 206c still remain as the functional portion of gas sensor chips 200a, 200b, or 200c. In such embodiments, gas sensor chips 200a, 200b, or 200c may be referred to as substrate free gas sensor chips or gas sensor chips having no substrate.

FIG. 2G illustrates a processing stage or step including the structure of FIG. 2F with the addition of lid membrane 226. According to various embodiments, lid membrane 226 is formed over embedding material 212 and cavities 224a, 224b, and 224c. In such embodiments, lid membrane 226 is patterned to form openings 228 to expose cavities 224a, 224b, and 224c and gas sensing regions 206a, 206b, and 206c. Lid membrane 226 is formed of a semiconductor material, such as silicon, in some embodiments. In other embodiments, lid membrane 226 may be formed of glass, such as silicon dioxide for example. In both such embodiments, a metal layer may be deposited on the semiconductor or oxide layer as a shielding. In further embodiments, lid membrane 226 is formed using a plastic material or a mold compound. In other embodiments, lid membrane 226 is formed using a metal, a metalized plastic, or a composite material.

FIG. 2H illustrates a processing stage or step including the structure of FIG. 2G illustrating an additional contact pad 221 formed in structural material 222. According to various embodiments, contact pad 220 and contact pad 221 may be formed to provide electrical contact to various components in a completed package. Contact pad 220 may be formed at the time RDL 214 is formed. In further embodiments, contact pad 221 is formed by patterning a portion of structural material 222 and depositing contact pad 221. In such embodiments, contact pad 221 may be formed in a similar manner as contact pad 220 and may include any of the same materials as described hereinabove in reference to contact pad 220. In various embodiments, contact pad 221 is formed after substrates 204a, 204b, and 204c are removed. Further, contact pad 221 may be specifically designated to identify contact pads used to provide an electrical connection to heating elements in gas sensing regions 206a, 206b, and 206c.

Figure 2I:
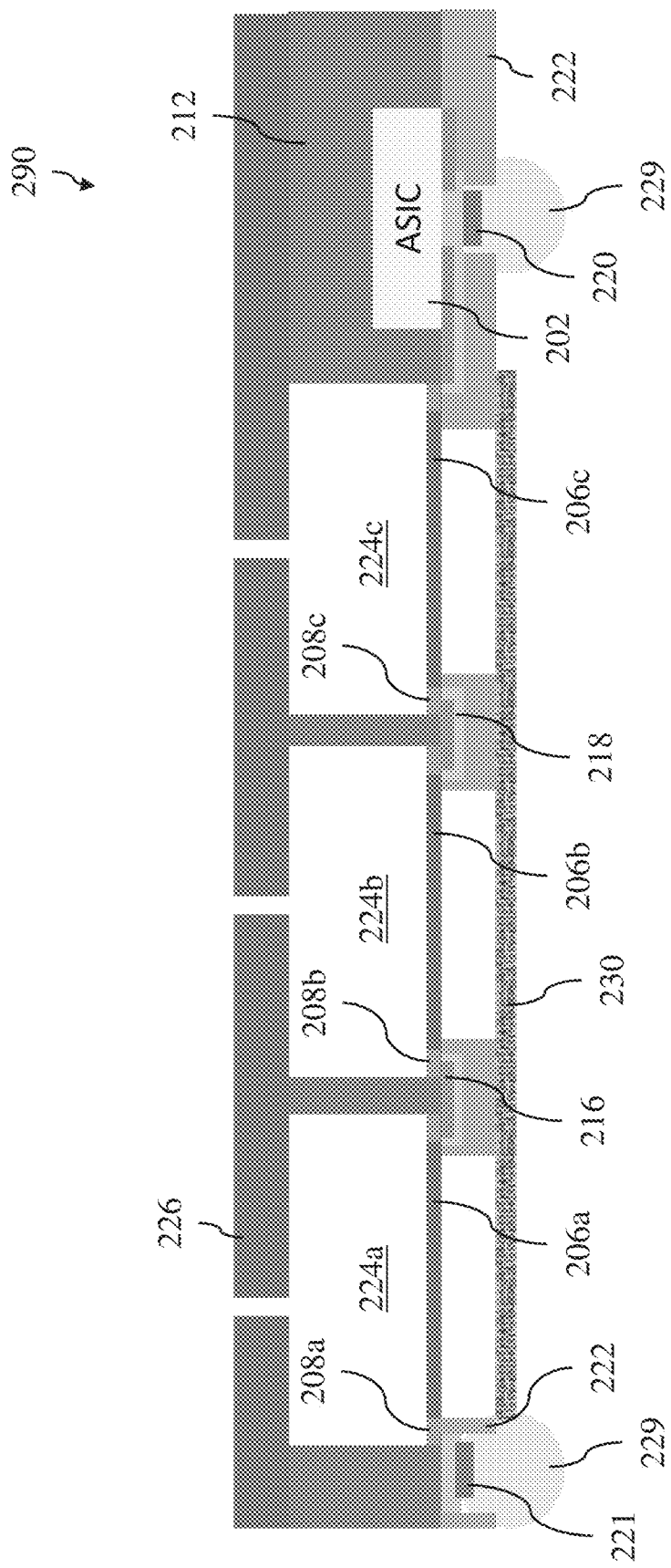

FIG. 2I illustrates a final processing stage or step including packaged gas sensor device 290. According to various embodiments, packaged gas sensor device 290 includes the structure of FIG. 2H with the addition of solder balls 229 and media separation membrane 230. In such embodiments, packaged gas sensor device 290 is an eWLB package that may be included in a system for integration with the gas sensor functionality of packaged gas sensor device 290. For example, packaged gas sensor device 290 may be attached to a printed circuit board (PCB) of a cellular phone, tablet computer, laptop, smart home device, or automotive component in various embodiments.

According to various embodiments, solder balls 229 may be arranged as a ball grid array (BGA) or a land grid array (LGA). In some embodiments, media separation membrane 230 is a gas permeable, liquid impermeable membrane. For example, media separation membrane 230 is a hydrophobic, oleophobic, or lipophobic mesh that is permeable to gas. In some embodiments, media separation membrane 230 is a polymer mesh with small openings with diameters much smaller than liquid water drops. For example, media separation membrane 230 may be a gore-tex fabric. In other embodiments, media separation membrane 230 is omitted.

As described hereinabove, packaged gas sensor device 290 is a packaged device that is substrate free or does not include a substrate in relation to gas sensing regions 206a, 206b, and 206c. Instead, packaged gas sensor device 290 includes cavities 224a, 224b, and 224c in embedding material 212 and gas sensing regions 206a, 206b, and 206c are directly supported by embedding material 212. In such embodiments, the absence of semiconductor substrates near gas sensing regions 206a, 206b, and 206c may improve heating of the gas sensitive layers using integrated heaters in gas sensing regions 206a, 206b, and 206c by reducing the thermal capacity due to removing semiconductor substrates near gas sensing regions 206a, 206b, and 206c. In such embodiments, ASIC 202 is embedded in embedding material 212 and may include a substrate, such as a semiconductor substrate, but gas sensing regions 206a, 206b, and 206c are substrate free or do not include a substrate.

Various embodiments include modifications to the process and structure described hereinabove in reference to FIGS. 2A-2I. Some of such embodiment modifications are described hereinafter in reference to the other figures. Description of materials, layers, or processing steps included hereinabove in reference to commonly numbered reference labels also applies hereinafter and is not repeated in the interest of brevity.

FIGS. 3A, 3B, 3C, 3D, 3E, and 3F illustrate cross-sectional views of processing stages for an embodiment packaged device. FIG. 3A illustrates a processing stage or step including substrates 204a, 204b, and 204c and ASIC 202. In such embodiments, substrates 204a, 204b, and 204c may be provided as dummy substrates without gas sensor components, for example. Other details described hereinabove in reference to FIG. 2A apply to the commonly numbered elements of the structure of FIG. 3A. Specifically, substrates 204a, 204b, and 204c may include any of the materials as described hereinabove. In particular embodiments, when substrates 204a, 204b, and 204c are provided as dummy substrates, substrates 204a, 204b, and 204c may be formed of any sacrificial material that is able to be removed using a selective removal, such as a selective etch, for example, with carrier substrate 210 and embedding material 212. For example, as described hereinabove, substrates 204a, 204b, and 204c may be formed of non-semiconducting materials, such as polymer based materials or metals. In a particular embodiment, substrates 204a, 204b, and 204c are formed of a structurable photoresist. In another embodiment, substrates 204a, 204b, and 204c are formed of a water-soluble material.

FIG. 3B illustrates a processing stage or step including carrier substrate 210, embedding material 212, substrates 204a, 204b, and 204c, and ASIC 202. Details described hereinabove in reference to FIG. 2B apply to the commonly numbered elements of the structure of FIG. 3B.

FIG. 3C illustrates a processing stage or step including isolation layer 234 and conductive layer 236 as portions of RDL 232 formed on embedding material 212 and providing electrical coupling to ASIC 202. According to various embodiments, RDL 232 may be formed in order to include gas sensors in portions of RDL 232. In such embodiments, substrates 204a, 204b, and 204c are dummy substrates and the structure of the gas sensors is formed during the process of forming RDL 232. Thus, the processing of RDL 232 proceeds in order to form gas sensitive regions, isolation regions, and heating elements.

According to various embodiments, isolation layer 234 is an electrically insulating layer. Isolation layer 234 includes any of the materials described hereinabove in reference to isolation layer 216 in FIGS. 2C-2I. In various embodiments, conductive layer 236 is formed on isolation layer 234 and patterned, such as by using a lithographic process, to form patterned regions 238a, 238b, and 238c. In such embodiments, patterned regions 238a, 238b, and 238c in conductive layer 236 form heating elements for the gas sensor structures. Patterned regions 238a, 238b, and 238c may include serpentine, or similar, resistive structures in some embodiments. Conductive layer 236 includes any of the materials described hereinabove in reference to conductive layer 218 in FIGS. 2C-2I.

FIG. 3D illustrates a processing stage or step including isolation layer 240 and conductive layer 242 as additional portions of RDL 232. According to various embodiments, isolation layer 240 is an electrically insulating layer. Isolation layer 240 includes any of the materials described hereinabove in reference to isolation layer 216 in FIGS. 2C-2I. In various embodiments, conductive layer 242 is formed on isolation layer 240 and patterned, such as by using a lithographic process, to form patterned regions 244a, 244b, and 244c. In such embodiments, patterned regions 244a, 244b, and 244c in conductive layer 242 form sensing elements for the gas sensor structures. Patterned regions 244a, 244b, and 244c may include alternating sensing fingers or similar interdigitated sensing structures. Conductive layer 242 includes any of the materials described hereinabove in reference to conductive layer 218 in FIGS. 2C-2I.

In various embodiments, the heating elements for the gas sensor structures provided as patterned regions 238a, 238b, and 238c in conductive layer 236 heat the sensing elements provided as patterned regions 244a, 244b, and 244c in conductive layer 242 when a current is provided through patterned regions 238a, 238b, and 238c. In such embodiments, isolation layer 240 provides electrical insulation between conductive layer 236 and conductive layer 242.

According to some embodiments, substrates 204a, 204b, and 204c may be removed following the processing stage or step of FIG. 3D (not shown). In such embodiments, when substrates 204a, 204b, and 204c are formed of a sacrificial material, such as a structurable photoresist, that can be selectively removed, release holes may be formed in RDL 232 and substrates 204a, 204b, and 204c are removed by selective etching or dissolving.

FIG. 3E illustrates a processing stage or step including the structure of FIG. 3D with the addition of solder balls 246 and solder balls 248. According to various embodiments, solder balls 246 may include any number of solder balls (note only a single solder ball 246 is shown) that contact conductive layer 236. In such embodiments, solder balls 246 may provide electrical contact to ASIC 202 and to the heating elements formed in portions of conductive layer 236. Similarly, solder balls 248 may include any number of solder balls (note only a single solder ball 248 is shown) that contact conductive layer 242. In such embodiments, solder balls 248 may provide electrical contact to the sensing elements formed in portions of conductive layer 242. According to various embodiments, solder balls 246 and solder balls 248 may be arranged as a BGA or a LGA.

FIG. 3F illustrates a final processing stage or step including packaged gas sensor device 292. According to various embodiments, packaged gas sensor device 292 includes the structure of FIG. 3E after embedding material 212 has been thinned from the topside (in relation to the illustrated figure), after a selective etch has been applied to remove substrates 204a, 204b, and 204c and form cavities 224a, 224b, and 224c in embedding material 212, and after forming gas sensitive regions 252a, 252b, and 252c. In such embodiments, packaged gas sensor device 292 is an eWLB package including gas sensors 250a, 250b, and 250c that may be included in a system for integration with the gas sensor functionality of packaged gas sensor device 292. For example, packaged gas sensor device 292 may be attached to a printed circuit board (PCB) of a cellular phone, tablet computer, laptop, smart home device, or automotive component in various embodiments. According to various embodiments, embedding material 212 may be removed as described hereinabove in reference to FIG. 2E and substrates 204a, 204b, and 204c may be removed as described hereinabove in reference to FIG. 2F. As described hereinabove in reference to FIG. 3D, substrates 204a, 204b, and 204c may alternatively be removed through release holes formed in RDL 232 in alternative embodiments. In such alternative embodiments, the thinning of embedding material 212 may be omitted.

In various embodiments, gas sensors 250a, 250b, and 250c are formed of isolation layer 234, conductive layer 236 (with patterned regions 238a, 238b, and 238c), isolation layer 240, conductive layer 242 (patterned regions 244a, 244b, and 244c), and gas sensitive regions 252a, 252b, and 252c. In such embodiments, gas sensitive regions 252a, 252b, and 252c may include materials that are sensitive to different gas concentrations. In particular embodiments, gas sensitive regions 252a, 252b, and 252c are formed of graphene that is functionalized with metal oxide nanoparticles. In still more particular embodiments, gas sensitive regions 252a, 252b, and 252c are formed of carbon nanotubes (CNTs) that are functionalized with metal oxide nanoparticles. In other embodiments, gas sensitive regions 252a, 252b, and 252c are formed of metal oxides directly. In the various embodiments, the metal oxides used to implement gas sensitive regions 252a, 252b, and 252c include tin dioxide ($SnO_2$), gallium oxide ($Ga_2O_3$), zinc oxide (ZnO), tungsten trioxide ($WO_3$), vanadium pentoxide ($V_2O_5$), or cobalt (II,III) oxide ($Co_3O_4$). In some other embodiments, other oxides of these materials may be used. In further alternative embodiments, other material oxides may also be used.

In various embodiments, a different functionalized material, such as the oxides described hereinabove, may be included in each of gas sensitive regions 252a, 252b, and 252c such that gas sensitive regions 252a, 252b, and 252c are each sensitive to a different type of gas concentration. As described hereinabove in reference to gas sensor chips 200a, 200b, and 200c in FIG. 2A, any number of gas sensors may be included, such as more than three or less than the three gas sensors 250a, 250b, and 250c. Thus, in various embodiments, packaged gas sensor device 292 may include three, five, eight, ten, twelve, sixteen, or twenty-four, for example, gas sensors sensitive to a same gas or different gases. In such embodiments, the gas sensors may include redundant sensors (where two or more gas sensors in packaged gas sensor device 292 are sensitive to the same gas concentration) or variety sensors (where each of the gas sensors in packaged gas sensor device 292 is sensitive to a different gas concentration).

Thus, according to various embodiments, gas sensors 250a, 250b, and 250c are formed below cavities 224a, 224b, and 224c, respectively, directly in RDL 232 of packaged gas sensor device 292. Although some of the materials and processes for forming gas sensors 250a, 250b, and 250c have been presented herein, further structures and methods for gas sensing elements are described in U.S. application Ser. No. 14/751,660 and U.S. application Ser. No. 14/749,102, as incorporated hereinabove. Various modifications and combinations of such gas sensing elements with embodiment methods and structures for gas sensors, such as gas sensors 250a, 250b, and 250c in RDL 232, are envisioned in the various embodiments.

In some embodiments, packaged gas sensor device 292 does not include a lid membrane covering cavities 224a, 224b, and 224c or a media separation membrane below gas sensitive regions 252a, 252b, and 252c (as illustrated in FIG. 3F). In other embodiments, packaged gas sensor device 292 includes lid membrane 226 (not shown) or media separation membrane 230 (not shown) as described hereinabove in reference to packaged gas sensor device 290 in FIG. 2I.

FIGS. 4A, 4B, 4C, 4D, 4E, and 4F illustrate cross-sectional views of processing stages for an embodiment packaged device. FIG. 4A illustrates a processing stage or step including substrates 204a, 204b, and 204c and ASIC 202. In such embodiments, substrates 204a, 204b, and 204c may be provided as dummy substrates without gas sensor components, for example. In various embodiments, stop layers 256a, 256b, and 256c are formed on bottom surfaces (in relation to the illustrated figure) of substrates 204a, 204b, and 204c, respectively. Stop layers 256a, 256b, and 256c may include an oxide or a nitride, such as silicon oxide or silicon nitride, for example. In other embodiments, stop layers 256a, 256b, and 256c include carbon. Other details described hereinabove in reference to FIG. 2A apply to the commonly numbered elements of the structure of FIG. 3A.

FIG. 4B illustrates a processing stage or step including carrier substrate 210, embedding material 212, substrates 204a, 204b, and 204c, and ASIC 202. Details described hereinabove in reference to FIG. 2B apply to the commonly numbered elements of the structure of FIG. 4B.

FIG. 4C illustrates a processing stage or step including isolation layer 234 and conductive layer 236 as portions of RDL 232 formed on embedding material 212 and providing electrical coupling to ASIC 202. Details described hereinabove in reference to FIGS. 2C and 3C apply to the commonly numbered elements of the structure of FIG. 4C with the addition of patterning modifications for isolation layer 234 and conductive layer 236.

According to various embodiments, isolation layer 234 is patterned to form openings 258a, 258b, and 258c, which expose stop layers 256a, 256b, and 256c, respectively. After patterning isolation layer 234, conductive layer 236 is formed and patterned, such as by using a lithographic process, to form patterned regions 260a, 260b, and 260c. In such embodiments, patterned regions 260a, 260b, and 260c in conductive layer 236 form sensing elements for the gas sensor structures. Patterned regions 260a, 260b, and 260c may include alternating sensing fingers or similar interdigitated sensing structures. Thus, the gas sensor structures of FIGS. 4A-4F are formed with the gas sensitive regions facing upwards (in relation to the illustrated figure), as opposed to the gas sensor structures of FIGS. 3A-3F, which are formed with the gas sensitive regions facing downwards (in relation to the illustrated figure).

FIG. 4D illustrates a processing stage or step including isolation layer 240, conductive layer 242, and isolation layer 264 as additional portions of RDL 232. According to various embodiments, conductive layer 242 is formed on isolation layer 240 and patterned, such as by using a lithographic process, to form patterned regions 262a, 262b, and 262c. In such embodiments, patterned regions 262a, 262b, and 262c in conductive layer 242 form heating elements for the gas sensor structures. Patterned regions 262a, 262b, and 262c may include serpentine, or similar, resistive structures in some embodiments.

In various embodiments, the heating elements for the gas sensor structures provided as patterned regions 262a, 262b, and 262c in conductive layer 242 heat the sensing elements provided as patterned regions 260a, 260b, and 260c in conductive layer 236 when a current is provided through patterned regions 262a, 262b, and 262c. In such embodiments, isolation layer 240 provides electrical insulation between conductive layer 236 and conductive layer 242. Further, isolation layer 264 is formed on conductive layer 242 and provides additional electrical insulation and protection for the heating elements for the gas sensor structures provided as patterned regions 262a, 262b, and 262c in conductive layer 242. Isolation layer 264 includes any of the materials described hereinabove in reference to isolation layer 216 in FIGS. 2C-2I.

FIG. 4E illustrates a processing stage or step including the structure of FIG. 4D with the addition of solder balls 266 and solder balls 268. According to various embodiments, solder balls 266 may include any number of solder balls (note only a single solder ball 266 is shown) that contact conductive layer 236. In such embodiments, solder balls 246 may provide electrical contact to ASIC 202 and to the sensing elements formed in portions of conductive layer 236. Similarly, solder balls 268 may include any number of solder balls (note only a single solder ball 268 is shown) that contact conductive layer 242. In such embodiments, solder balls 268 may provide electrical contact to the heating elements formed in portions of conductive layer 242. According to various embodiments, solder balls 266 and solder balls 268 may be arranged as a BGA or an LGA.

FIG. 4F illustrates a final processing stage or step including packaged gas sensor device 294. According to various embodiments, packaged gas sensor device 294 includes the structure of FIG. 4E after embedding material 212 has been thinned from the topside (in relation to the illustrated figure), after a selective etch has been applied to remove substrates 204a, 204b, and 204c and form cavities 224a, 224b, and 224c in embedding material 212, after a selective etch has been applied to remove stop layers 256a, 256b, and 256c, and after forming gas sensitive regions 252a, 252b, and 252c. In such embodiments, packaged gas sensor device 294 is an eWLB package including gas sensors 270a, 270b, and 270c that may be included in a system for integration with the gas sensor functionality of packaged gas sensor device 294. For example, packaged gas sensor device 294 may be attached to a printed circuit board (PCB) of a cellular phone, tablet computer, laptop, smart home device, or automotive component in various embodiments.

According to various embodiments, embedding material 212 may be removed as described hereinabove in reference to FIG. 2E and substrates 204a, 204b, and 204c may be removed as described hereinabove in reference to FIG. 2F.

In various embodiments, stop layers 256a, 256b, and 256c are also etched using a selective etch process. In such embodiments, the selective etch process used for removing stop layers 256a, 256b, and 256c may be performed as described hereinabove in reference to FIG. 2F, but using a different etchant as the etchant for substrates 204a, 204b, and 204c. In various embodiments, the etchants used for substrates 204a, 204b, and 204c and for stop layers 256a, 256b, and 256c are selected based on the materials of the respective layers, as will be readily appreciated by those of skill in the art. Such etchants may include etchants for a wet chemical etch process, such as potassium hydroxide (KOH) or tetramethylammonium hydroxide (TMHA), for example, or for a dry (plasma) chemical etch process. Depending on the materials used for substrates 204a, 204b, and 204c or stop layers 256a, 256b, and 256c, solvents may also be used in some embodiments.

In various embodiments, after removing substrates 204a, 204b, and 204c and forming cavities 224a, 224b, and 224c, gas sensitive regions 252a, 252b, and 252c are formed on patterned regions 260a, 260b, and 260c of conductive layer 236 in cavities 224a, 224b, and 224c. In such embodiments, gas sensors 270a, 270b, and 270c are formed in RDL 232 and include the materials and features as described hereinabove in reference to gas sensors 250a, 250b, and 250c in FIG. 3F, but are oriented with gas sensitive regions 252a, 252b, and 252c arranged in cavities 224a, 224b, and 224c, respectively, on a topside of RDL 232 (in relation to the illustrated figure), as opposed to being arranged on a bottom side of the RDL 232 (in relation to the illustrated figure) for gas sensors 250a, 250b, and 250c.

In some embodiments, packaged gas sensor device 294 does not include a lid membrane covering cavities 224a, 224b, and 224c or a media separation membrane below isolation layer 264 (as illustrated in FIG. 4F). In other embodiments, packaged gas sensor device 294 includes lid membrane 226 (not shown) or media separation membrane 230 (not shown) as described hereinabove in reference to packaged gas sensor device 290 in FIG. 2I.

Figure 5I:
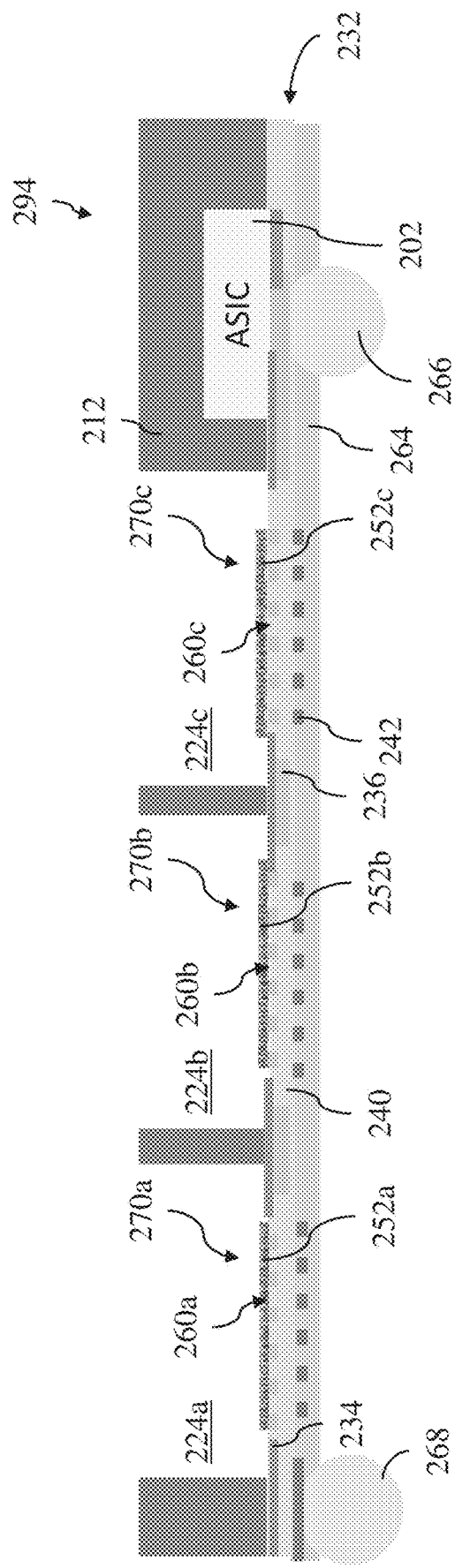

FIGS. 5A, 5B, 5C, 5D, 5E, 5F, 5G, 5H, and 5I illustrate cross-sectional views of processing stages for an embodiment packaged device. FIG. 5A illustrates a processing stage or step including substrates 204a, 204b, and 204c and ASIC 202. Details described hereinabove in reference to FIG. 4A apply to the commonly numbered elements of the structure of FIG. 5A.

FIG. 5B illustrates a processing stage or step including substrates 204a, 204b, and 204c attached to wafer 272 and placed on carrier substrate 210 (ASIC 202 is not illustrated in FIG. 5B). According to various embodiments, wafer 272 is used as a carrier wafer for arrangement and placement of substrates 204a, 204b, and 204c. In such embodiments, substrates 204a, 204b, and 204c may be formed or patterned on wafer 272 at a wafer layer. In other embodiments, substrates 204a, 204b, and 204c are attached to wafer 272 after being separately formed. Wafer 272 is formed of a same material as substrates 204a, 204b, and 204c. In other embodiments, wafer 272 is formed of a different material than substrates 204a, 204b, and 204c.

In various embodiments, wafer 272 provides a placement of substrates 204a, 204b, and 204c on carrier substrate 210 using a wafer level placement system. In such embodiments, the alignment of wafer 272 with carrier substrate 210 is done using a wafer level alignment process. During the wafer level alignment process, the positions and spatial relationships between substrates 204a, 204b, and 204c are maintained because of the physical attachment to wafer 272. Thus, substrates 204a, 204b, and 204c are arranged on carrier substrate 210 using a wafer level placement without using pick and place techniques, such as by using an SMT component placement system. In particular embodiments, the wafer level placement system may be less time consuming or cheaper compared to some pick and place techniques.

FIG. 5C illustrates a processing stage or step including the structure of FIG. 5B after removing wafer 272 (ASIC 202 is not illustrated in FIG. 5C). According to various embodiments, wafer 272 removed through a wafer thinning process. The wafer thinning process includes a CMP from the topside (in relation to the illustrated figure). In other embodiments, the wafer thinning process includes a selective wet etch. Once wafer 272 is removed, the arrangement of substrates 204a, 204b, and 204c on carrier substrate 210 is complete.

FIG. 5D illustrates a processing stage or step including the structure of FIG. 5C with ASIC 202 attached to carrier substrate 210. ASIC 202 is attached to carrier substrate 210 using a pick and place technique, such as by using an SMT component placement system. In such embodiments, ASIC 202 may include only a single semiconductor die for placement on carrier substrate 210. Thus, the placement effort for ASIC 202 may be small compared to substrates 204a, 204b, and 204c, which may include any number of substrate chips (although only three are illustrated), as described hereinabove in reference to the other figures. In alternative embodiments, ASIC 202 may include more than one semiconductor die placed on carrier substrate 210.

FIG. 5E illustrates a processing stage or step including carrier substrate 210, embedding material 212, substrates 204a, 204b, and 204c, and ASIC 202. Details described hereinabove in reference to FIG. 4B apply to the commonly numbered elements of the structure of FIG. 5E.

FIG. 5F illustrates a processing stage or step including isolation layer 234 and conductive layer 236 as portions of RDL 232 formed on embedding material 212 and providing electrical coupling to ASIC 202. Details described hereinabove in reference to FIG. 4C apply to the commonly numbered elements of the structure of FIG. 5F.

FIG. 5G illustrates a processing stage or step including isolation layer 240, conductive layer 242, and isolation layer 264 as additional portions of RDL 232. Details described hereinabove in reference to FIG. 4D apply to the commonly numbered elements of the structure of FIG. 5G.

FIG. 5H illustrates a processing stage or step including the structure of FIG. 5G with the addition of solder balls 266 and solder balls 268. Details described hereinabove in reference to FIG. 4E apply to the commonly numbered elements of the structure of FIG. 5H.

FIG. 5I illustrates a final processing stage or step including packaged gas sensor device 294. Details described hereinabove in reference to FIG. 4F apply to the commonly numbered elements of the structure of FIG. 5I. According to various embodiments, FIGS. 5A-5I illustrate processing stages for packaged gas sensor device 294 as described hereinabove in reference to FIGS. 4A-4F, where placement of substrates 204a, 204b, and 204c has been accomplished using wafer 272 in place of pick and place techniques. In further embodiments, the process for forming packaged gas sensor device 290, as described hereinabove in reference to FIGS. 2A-2I, or the process for forming packaged gas sensor device 292, as described hereinabove in reference to FIG. 3A-3F, may similarly be modified to include wafer 272 for the placement of substrates 204a, 204b, and 204c.

According to various embodiments, packaged gas sensor device 290, packaged gas sensor device 292, and packaged gas sensor device 294, as described hereinabove in reference to FIGS. 2A-2I, 3A-3F, 4A-4F, and 5A-5I, are various embodiment implementations of packaged device 100 with MEMS sensor 102 and ASIC 104, as described hereinabove in reference to FIG. 1.

Figure 6:
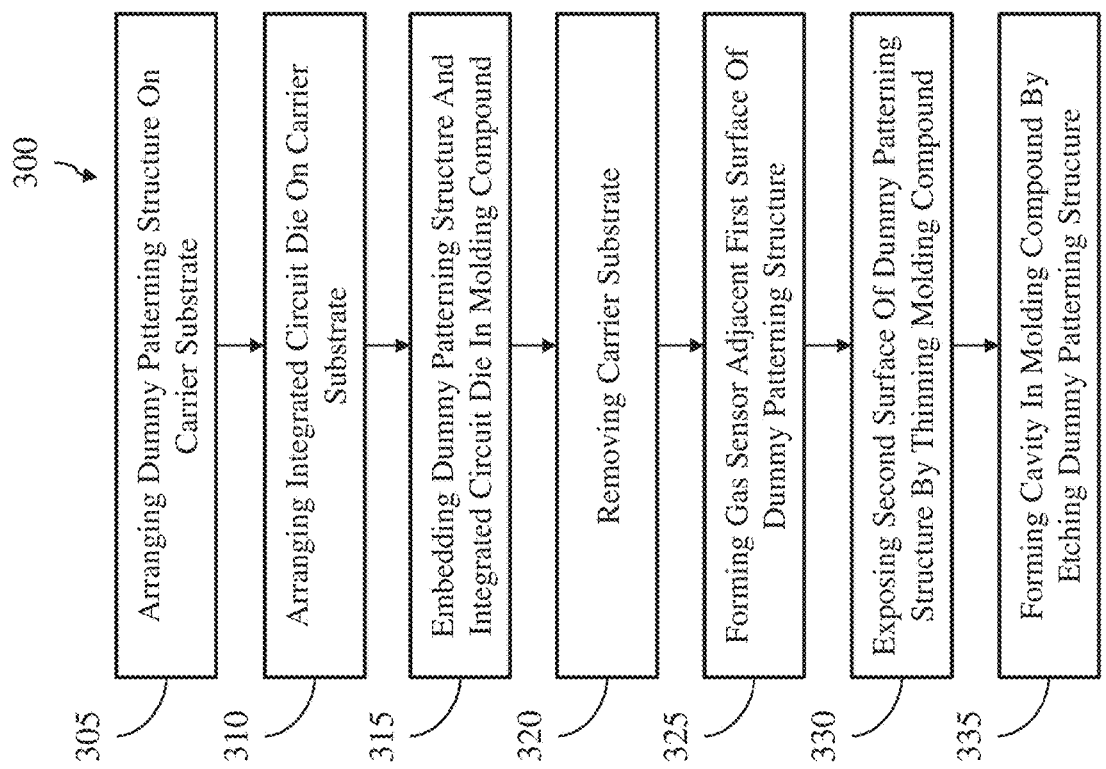
FIG. 6 illustrates a flowchart diagram of an embodiment method of forming an embodiment packaged device.

FIG. 6 illustrates a flowchart diagram of an embodiment method 300 of forming an embodiment packaged device. According to various embodiments, method 300 includes steps 305, 310, 315, 320, 325, 330, and 335. Step 305 includes arranging a dummy patterning structure on a carrier substrate. The dummy patterning structure is a semiconductor substrate, for example. Step 310 includes arranging an integrated circuit (IC) die on the carrier substrate. The IC die may be an ASIC die. Following step 310, step 315 includes embedding the dummy patterning structure and the IC die in molding compound. For example, the dummy patterning structure and the IC die may be embedding through an eWLB process that forms a reconstituted wafer package.

According to various embodiments, step 320 includes removing the carrier substrate. Step 325 includes forming a gas sensor adjacent a first surface of the dummy patterning structure. The gas sensor may be formed in an RDL at the first surface. In different embodiments, the gas sensor is formed with gas sensitive materials facing the dummy patterning structure or facing away from the dummy patterning structure. Step 330 includes exposing a second surface of the dummy patterning structure by thinning the molding compound. The second surface is opposite the first surface. Step 335 includes forming a cavity in the molding compound by etching the dummy patterning structure. For example, the dummy patterning structure is removed using a selective wet or dry etch.

In various embodiments, method 300 may be modified to include additional steps or the steps may be performed in a different order. In further embodiments, any number of cavities and gas sensors may be formed for the embodiment packaged device of method 300. For example, two, four, five, eight, ten, twelve, sixteen, twenty, twenty-four, or more gas sensors and corresponding cavities may be formed.

Figure 7:
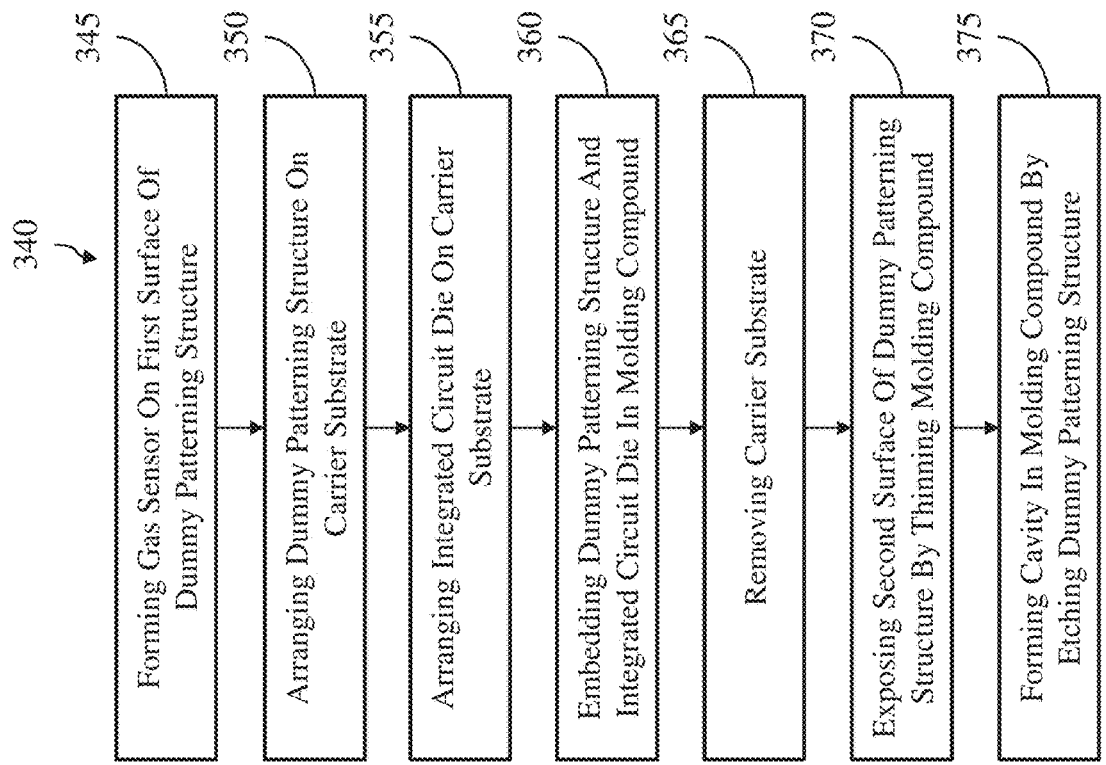
FIG. 7 illustrates a flowchart diagram of another embodiment method of forming another embodiment packaged device.

FIG. 7 illustrates a flowchart diagram of another embodiment method 340 of forming another embodiment packaged device. According to various embodiments, method 340 includes steps 345, 350, 355, 360, 365, 370, and 375. Step 345 includes forming a gas sensor on a first surface of a dummy patterning structure. The dummy patterning structure is a semiconductor substrate, for example. Step 350 includes arranging the dummy patterning structure on a carrier substrate. Following step 350, step 355 includes arranging an IC die on the carrier substrate. The IC die may be an ASIC die.

According to various embodiments, step 360 includes embedding the dummy patterning structure and the IC die in molding compound. For example, the dummy patterning structure and the IC die may be embedding through an eWLB process that forms a reconstituted wafer package. Step 365 includes removing the carrier substrate. Further, step 370 includes exposing a second surface of the dummy patterning structure by thinning the molding compound. The second surface is opposite the first surface. Step 375 includes forming a cavity in the molding compound by etching the dummy patterning structure. For example, the dummy patterning structure is removed using a selective wet or dry etch.

In various embodiments, method 340 may be modified to include additional steps or the steps may be performed in a different order. In further embodiments, any number of cavities and gas sensors may be formed for the embodiment packaged device of method 340. For example, two, four, five, eight, ten, twelve, sixteen, twenty, twenty-four, or more gas sensors and corresponding cavities may be formed.

According to an embodiment, a sensor package includes an electrically insulating substrate including a cavity in the electrically insulating substrate, an ambient sensor, an integrated circuit die embedded in the electrically insulating substrate, and a plurality of conductive interconnect structures coupling the ambient sensor to the integrated circuit die. The ambient sensor is supported by the electrically insulating substrate and arranged adjacent the cavity. Other embodiments include corresponding systems and apparatus, each configured to perform various embodiment methods.

In various embodiments, the cavity includes a plurality of cavities in the electrically insulating substrate, the ambient sensor includes a plurality of ambient sensors, where each ambient sensor of the plurality of ambient sensors is supported by the electrically insulating substrate and arranged adjacent a cavity of the plurality of cavities, and the plurality of conductive interconnect structures couples the plurality of ambient sensors to the integrated circuit die.

In various embodiments, the plurality of ambient sensors includes a plurality of gas sensors. In some embodiments, each gas sensor of the plurality of gas sensors includes a gas sensitive layer exposed to a cavity of the plurality of cavities. Further, each cavity of the plurality of cavities may extend through the electrically insulating substrate from a first surface of the electrically insulating substrate to a second surface of the electrically insulating substrate, where the first surface is opposite the second surface. In additional embodiments, the sensor package further includes a lid layer on the first surface of the electrically insulating substrate covering the plurality of cavities, where the lid layer includes a plurality of openings fluidically coupled to the plurality of cavities and where the plurality of ambient sensors is arranged at the second surface of the electrically insulating substrate. In such embodiments, the plurality of openings may include hydrophobic openings.

In various embodiments, the electrically insulating substrate includes molding compound. In other embodiments, the electrically insulating substrate includes glass or ceramic. In some embodiments, the sensor package further includes a structural support layer on the plurality of conductive interconnect structures. The sensor package may further include a plurality of contact pads coupled to the plurality of conductive interconnect structures, and a plurality of solder elements coupled to the plurality of contact pads. In some such embodiments, the solder elements are arranged as a ball grid array (BGA) or a land grid array (LGA). In further embodiments, the sensor package further includes a gas permeable membrane covering the plurality of ambient sensors, where the gas permeable membrane includes a hydrophobic structure.

According to an embodiment, a method of forming a sensor package includes arranging a dummy patterning structure on a carrier substrate, arranging an integrated circuit die on the carrier substrate, embedding the dummy patterning structure and the integrated circuit die in an electrically insulating material, removing the carrier substrate, forming an ambient sensor adjacent a first surface of the dummy patterning structure, exposing a second surface of the dummy patterning structure by thinning the electrically insulating material, and forming a cavity in the electrically insulating material by etching the dummy patterning structure. The second surface of the dummy patterning structure is opposite the first surface of the dummy patterning structure. Other embodiments include corresponding systems and apparatus, each configured to perform various embodiment methods.

In various embodiments, forming the ambient sensor includes forming a gas sensor. In some embodiments, forming a gas sensor includes forming a gas sensor with a gas sensitive layer facing the dummy patterning structure. In other embodiments, forming a gas sensor includes forming a gas sensor with a gas sensitive layer facing away from the dummy patterning structure.

In various embodiments, arranging a dummy patterning structure on the carrier substrate includes arranging a plurality of dummy patterning structures on the carrier substrate, forming a gas sensor adjacent a first surface of the dummy patterning structure includes forming a plurality of gas sensors, and forming a cavity in the electrically insulating material by etching the dummy patterning structure includes forming a plurality of cavities in the electrically insulating material by etching the plurality of dummy patterning structures. In such embodiments, each gas sensor of the plurality of gas sensors is formed adjacent a first surface of a dummy patterning structure of the plurality of dummy patterning structures. In some embodiments, each dummy patterning structure of the plurality of dummy patterning structures includes a silicon dummy substrate. In further embodiments, arranging the plurality of dummy patterning structures on the carrier substrate includes placing each dummy patterning structure of the plurality of dummy patterning structures using a pick and place technique. In still further embodiments, arranging the plurality of dummy patterning structures on the carrier substrate includes patterning a dummy wafer with a dummy pattern, placing the dummy wafer on the carrier substrate, and thinning the dummy wafer to form the plurality of dummy patterning structures on the carrier substrate.

In various embodiments, forming the gas sensor includes forming a heating element, forming an electrically insulating layer, forming an electrically conductive structure on the electrically insulating layer, and forming a gas sensitive layer on the electrically conductive structure. In some embodiments, the method further includes forming a plurality of conductive interconnect structures coupled to the ambient sensor and the integrated circuit die. The method may further include forming a lid layer covering the cavity in the electrically insulating material, where the lid layer includes an opening connected to the cavity.

In various embodiments, embedding the dummy patterning structure and the integrated circuit die in the electrically insulating material includes embedding the dummy patterning structure and the integrated circuit die in molding compound. In some embodiments, embedding the dummy patterning structure and the integrated circuit die in molding compound includes forming a reconstituted wafer using an embedded wafer level ball grid array (eWLB) process. In other embodiments, embedding the dummy patterning structure and the integrated circuit die in the electrically insulating material includes embedding the dummy patterning structure and the integrated circuit die in glass or ceramic.

According to an embodiment, a method of forming a sensor package includes forming an ambient sensor on a first surface of a dummy patterning structure, arranging the dummy patterning structure on a carrier substrate, arranging an integrated circuit die on the carrier substrate, embedding the dummy patterning structure and the integrated circuit die in electrically insulating material, removing the carrier substrate, exposing a second surface of the dummy patterning structure by thinning the electrically insulating material, and forming a cavity in the electrically insulating material by etching the dummy patterning structure. The second surface of the dummy patterning structure is opposite the first surface of the dummy patterning structure. Other embodiments include corresponding systems and apparatus, each configured to perform various embodiment methods.

In various embodiments, the method further includes forming a lid layer covering the cavity in the electrically insulating material, where the lid layer includes an opening connected to the cavity. In some embodiments, forming the ambient sensor includes forming a gas sensor. In additional embodiments, forming a gas sensor on a first surface of a dummy patterning structure includes forming a plurality of gas sensors, arranging the dummy patterning structure on the carrier substrate includes arranging the plurality of dummy patterning structures on the carrier substrate, and forming a cavity in the electrically insulating material by etching the dummy patterning structure includes forming a plurality of cavities in the electrically insulating material by etching the plurality of dummy patterning structures. In such embodiments, each gas sensor of the plurality of gas sensors is formed on a first surface of a dummy patterning structure of a plurality of dummy patterning structures. In further embodiments, each dummy patterning structure of the plurality of dummy patterning structures includes a silicon dummy substrate.

In various embodiments, embedding the dummy patterning structure and the integrated circuit die in the electrically insulating material includes embedding the dummy patterning structure and the integrated circuit die in molding compound. In such embodiments, embedding the dummy patterning structure and the integrated circuit die in molding compound may include forming a reconstituted wafer using an embedded wafer level ball grid array (eWLB) process. In other embodiments, embedding the dummy patterning structure and the integrated circuit die in the electrically insulating material includes embedding the dummy patterning structure and the integrated circuit die in glass or ceramic.

Advantages of various embodiments described herein may include packaged gas sensor devices without substrates adjacent heating elements, leading to decreased thermal capacity and improved thermal performance. Further advantages of various embodiments may include small packaged size, low processing costs, and robustness packaged devices.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method of forming a sensor package, the method comprising:
    forming an ambient sensor on a first surface of a dummy patterning structure;
    arranging the dummy patterning structure on a carrier substrate after forming the ambient sensor;
    arranging an integrated circuit die on the carrier substrate;
    embedding the dummy patterning structure and the integrated circuit die in electrically insulating material;
    removing the carrier substrate;
    exposing a second surface of the dummy patterning structure by thinning the electrically insulating material, the second surface opposite the first surface; and forming a cavity in the electrically insulating material by etching the dummy patterning structure.

2. The method of claim 1, further comprising forming a lid layer covering the cavity in the electrically insulating material, the lid layer comprising an opening connected to the cavity.

3. The method of claim 1, wherein forming the ambient sensor comprises forming a gas sensor.

4. The method of claim 3, wherein
the dummy patterning structure comprises a plurality of dummy patterning structures;
forming the gas sensor comprises forming a plurality of gas sensors, each gas sensor of the plurality of gas sensors being formed on the first surface of at least one dummy patterning structure of the plurality of dummy patterning structures;
arranging the dummy patterning structure on the carrier substrate comprises arranging the plurality of dummy patterning structures on the carrier substrate; and
forming the cavity in the electrically insulating material comprises forming a plurality of cavities in the electrically insulating material by etching the plurality of dummy patterning structures.

5. The method of claim 4, wherein each dummy patterning structure of the plurality of dummy patterning structures comprises a silicon dummy substrate.

6. The method of claim 1, wherein embedding the dummy patterning structure and the integrated circuit die in the electrically insulating material comprises embedding the dummy patterning structure and the integrated circuit die in a molding compound.

7. The method of claim 6, wherein embedding the dummy patterning structure and the integrated circuit die in the molding compound comprises forming a reconstituted wafer using an embedded wafer level ball grid array (eWLB) process.

8. The method of claim 1, wherein embedding the dummy patterning structure and the integrated circuit die in the electrically insulating material comprises embedding the dummy patterning structure and the integrated circuit die in glass or ceramic.

9. A method of forming a sensor package, the method comprising:
forming a gas sensor comprising a top surface and a bottom surface, the top surface being opposite the bottom surface, wherein the gas sensor has a planar structure, and the entire top surface of the gas sensor is parallel to the entire bottom surface of the gas sensor;
forming embedding material adjacent to the gas sensor, wherein the top surface of the gas sensor and the embedding material form a boundary of a first cavity and the top surface of the gas sensor faces an unfilled void of the first cavity, wherein the bottom surface of the gas sensor forms a boundary of a second cavity and faces an unfilled void of the second cavity, and wherein a first integrated circuit die is enclosed in the embedding material;
forming a redistribution layer on the embedding material and electrically coupled to the first integrated circuit and to the gas sensor;
forming a lid membrane disposed over the gas sensor, the lid membrane having an opening extending from the first cavity through the lid membrane; and
forming a plurality of conductive interconnect structures coupling the gas sensor to the first integrated circuit die.

10. The method of claim 9, wherein:
the first cavity comprises a plurality of first cavities formed between the embedding material;
the gas sensor comprises a plurality of gas sensors, each gas sensor of the plurality of gas sensors forming a bottom boundary of the plurality of first cavities; and
the plurality of conductive interconnect structures couples the plurality of gas sensors to the first integrated circuit die.

11. The method of claim 10, wherein the second cavity comprises a plurality of second cavities, and the plurality of gas sensors forms a top boundary of the plurality of second cavities.

12. The method of claim 11, further comprising forming a gas permeable membrane disposed below the plurality of gas sensors, wherein the gas permeable membrane is a hydrophobic structure and forms a bottom boundary of the plurality of second cavities.

13. The method of claim 12, further comprising forming a plurality of contact pads coupled to the plurality of conductive interconnect structures; and
forming a plurality of solder elements coupled to the plurality of contact pads.

14. The method of claim 13, wherein forming the plurality of solder elements comprises forming a ball grid array (BGA) or a land grid array (LGA).

15. The method of claim 11, wherein the opening in the lid membrane comprises a plurality of openings fluidically coupled to the plurality of first cavities.

16. The method of claim 15, wherein the plurality of openings comprise hydrophobic openings.

17. The method of claim 9, wherein the embedding material comprises glass or ceramic material.

18. The method of claim 9, further comprising forming a gas permeable membrane disposed below the gas sensor, wherein the gas permeable membrane is a hydrophobic structure.

19. The method of claim 9, wherein forming the plurality of conductive interconnect structures comprises the forming the redistribution layer on the embedding material, wherein the redistribution layer comprises an insulation layer and a conductive layer that includes the plurality of conductive interconnect structures.

20. The method of claim 9, wherein forming the gas sensor comprises:
forming the gas sensor on a semiconductor substrate; and
removing the semiconductor substrate after forming the gas sensor, wherein the gas sensor is supported by the embedding material after the semiconductor substrate is removed.

21. A method of operating an ambient sensor package comprising a package structure formed of an electrically insulating embedding material, the package structure comprising a cavity in the electrically insulating embedding material and a redistribution layer disposed on a first side of the package structure and supported by the package structure; an ambient sensor configured to detect a presence of a gas, the ambient sensor comprising a first integrated circuit die disposed over the cavity and having edges supported by the redistribution layer, the first integrated circuit die comprising a first side facing an unfilled void in the cavity, a second side opposite the first side exposed by an aperture in the redistribution layer, and a gas sensing region disposed on the second side of the first integrated circuit die, wherein the entire first side of the first integrated circuit die is substantially parallel to the entire second side of the first integrated circuit die; and a second integrated circuit die embedded in the package structure, wherein a thickness of the first integrated circuit die is less than a thickness of the second integrated circuit die, and the second integrated circuit die is electrically coupled to the first integrated circuit die via the redistribution layer, the method comprising:

sensing a gas using the ambient sensor.

* * * * *